(12) United States Patent
Seliktar et al.

(10) Patent No.: US 9,492,376 B2
(45) Date of Patent: Nov. 15, 2016

(54) POLYMER-CONJUGATED ALBUMIN HYDROGELS FOR CONTROLLED RELEASE OF THERAPEUTIC AGENTS

(75) Inventors: Dror Seliktar, Haifa (IL); Liat Oss-Ronen, Zikhron-Yaakov (IL)

(73) Assignee: TECHNION RESEARCH AND DEVELOPMENT FOUNDATION LTD., Haifa (IL)

(*) Notice: Subject to any disclaimer, the term of this patent is extended or adjusted under 35 U.S.C. 154(b) by 14 days.

(21) Appl. No.: 13/133,241

(22) PCT Filed: Dec. 7, 2009

(86) PCT No.: PCT/IL2009/001154
§ 371 (c)(1),
(2), (4) Date: Jun. 7, 2011

(87) PCT Pub. No.: WO2010/064252
PCT Pub. Date: Jun. 10, 2010

(65) Prior Publication Data
US 2011/0238000 A1 Sep. 29, 2011

(30) Foreign Application Priority Data

Dec. 7, 2008 (IL) .......................................... 195764

(51) Int. Cl.
| | | |
|---|---|---|
| *A61K 38/38* | (2006.01) | |
| *A61K 47/42* | (2006.01) | |
| *A61K 9/00* | (2006.01) | |
| *A61K 47/48* | (2006.01) | |
| *A61K 31/37* | (2006.01) | |
| *A61K 9/22* | (2006.01) | |

(52) U.S. Cl.
CPC ............. *A61K 9/0024* (2013.01); *A61K 31/37* (2013.01); *A61K 47/42* (2013.01); *A61K 47/48784* (2013.01)

(58) Field of Classification Search
CPC .... A61K 38/38; A61K 38/385; C07K 14/76; C07K 14/765; C07K 14/77
See application file for complete search history.

(56) References Cited

U.S. PATENT DOCUMENTS

| | | | | |
|---|---|---|---|---|
| 5,733,563 | A * | 3/1998 | Fortier ........................... | 424/422 |
| 5,766,897 | A * | 6/1998 | Braxton ........................ | 435/463 |
| 2004/0009534 | A1* | 1/2004 | Sato et al. ..................... | 435/7.1 |
| 2005/0187139 | A1* | 8/2005 | Assaly et al. ..................... | 514/2 |

FOREIGN PATENT DOCUMENTS

| | | |
|---|---|---|
| WO | 95/15352 A1 | 6/1995 |
| WO | 2005/061018 A1 | 7/2005 |
| WO | 2008/126092 A2 | 10/2008 |

OTHER PUBLICATIONS

Gayet et al., "High Water content BSA-PEG hydrogel for controlled release device: Evaluation of the drug release properties", Journal of Controlled Release, 1998, pp. 177-184.*
Salmaso et al., "Site-selective protein glycation and PEGylation", European Polymer Journal, 2008, pp. 1378-1389.*
Dikovsky, et al., "The effect of structural alterations of PEG-fibrinogen hydrogel scaffolds on 3-D cellular morphology and cellular migration" Biomaterials 27 pp. 1496-1506, (2006).
Gayet et al., "Drug Release from New Bioartificial Hydrogel", Artificial Cells, Blood Substitutes and Biotechnology vol. 23, No. 5, pp. 605-611, (1995).
Gayet et al., "High water content BSA-PEG hydrogel for controlled release device: Evaluation of the drug release properties", Journal of Controlled Release vol. 38, Issues 2-3, pp. 177-184, (1996).
Gonen-Wadmany et al., "Protein-polymer conjugates for forming photopolymerizable biomimetic hydrogels for tissue engineering" Biomaterials vol. 28, No. 26., pp. 3876-3886, (2007).
Greenwald et al., "Effective drug delivery by PEGylated drug conjugates" Advanced Drug Delivery Reviews vol. 55 No. 2 pp. 217-250, (2003).
Huynh et al., "Functionalized injectable hydrogels for controlled insulin delivery" Biomaterials vol. 29, No. 16, pp. 2527-2534, (2008).
Iza et al., "Hydrogels of poly(ethylene glycol): mechanical characterization and release of a model drug" J Control Release No. 52 pp. 41-51, (1998).
Lutolf et al., "Synthesis and Physicochemical Characterization of End-Linked Poly(ethylene glycol)-co-peptide Hydrogels Formed by Michael-Type Addition" Biomacromolecules 4 pp. 713-722, (2003).
Nag et al., "A colorimetric assay for estimation of polyethylene glycol and polyethylene glycolated protein using ammonium ferrothiocyanate" Anal Biochem 237 pp. 224-231, (1996).
Peppas et al., "Hydrogels in pharmaceutical formulations" European Journal of Pharmaceutics and Biopharmaceutics 50 pp. 27-46, (2000).
Veronese et al., "PEGylation, successful approach to drug delivery" Drug Discovery Today vol. 10, Issue 21 pp. 1451-1458, (2005).
Wacker et al., "Delivery of sphingosine 1-phosphate from poly(ethylene glycol) hydrogels" Biomacromolecules. 7 pp. 1335-1343, (2006).

* cited by examiner

*Primary Examiner* — Lianko Garyu
(74) *Attorney, Agent, or Firm* — McDonnell Boehnen Hulbert & Berghoff LLP

(57) ABSTRACT

A hydrogel system comprising polymer-conjugated albumin molecules is provided for controlled release delivery of therapeutic agents. The polymer is a functionalized synthetic polymer, preferably PEG-diacrylate. The polymer-conjugated albumin is preferably mono-PEGylated albumin. The hydrogel system may comprise a matrix to which the polymer-conjugated albumin molecules are linked via a functional group of the polymer. The matrix may be formed from the same polymer of the polymer-albumin conjugate.

12 Claims, 9 Drawing Sheets

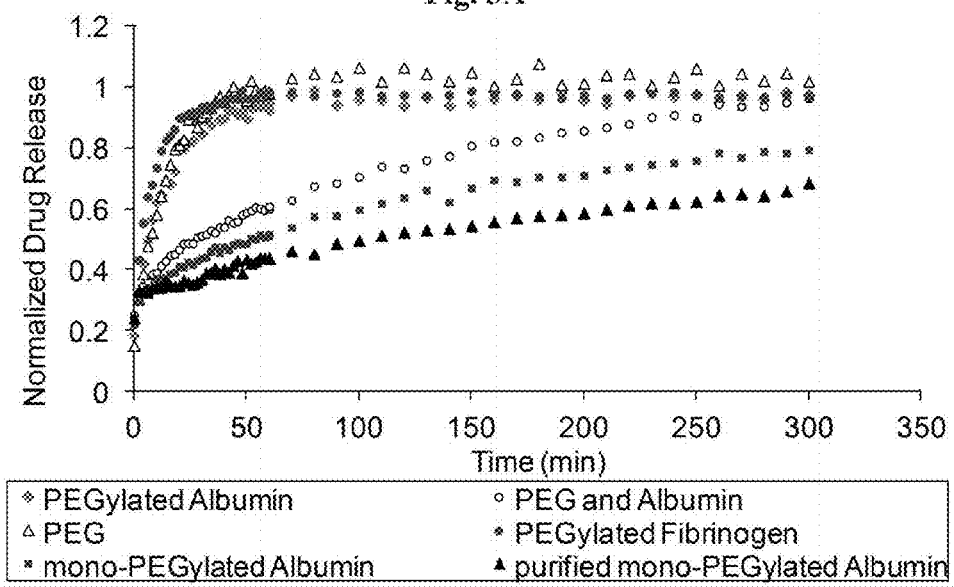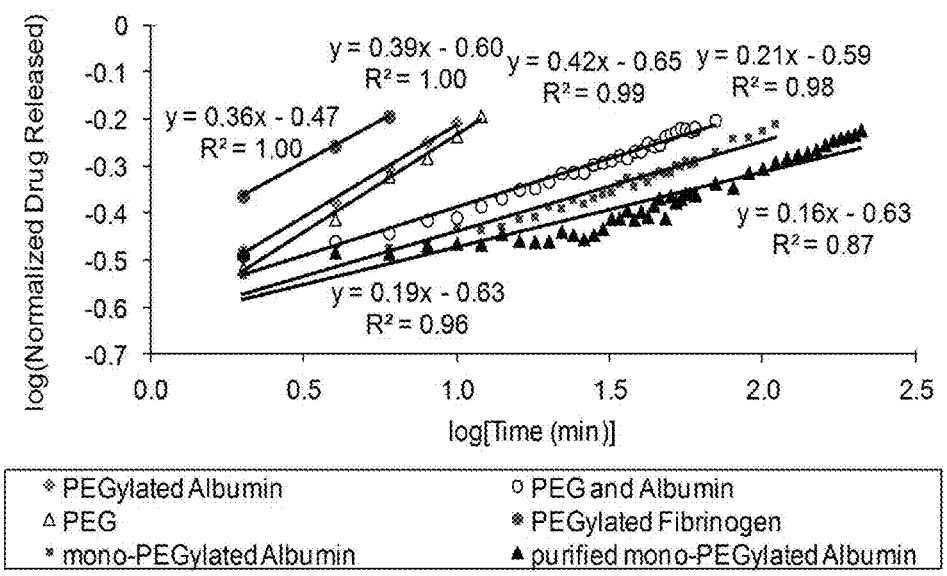

POLYMER-CONJUGATED ALBUMIN HYDROGELS FOR CONTROLLED RELEASE OF THERAPEUTIC AGENTS

FIELD OF THE INVENTION

The present invention relates to hydrogel systems comprising polymer-conjugated albumin molecules optionally linked to a matrix for controlled release of therapeutic agents, and to methods of generating same.

BACKGROUND OF THE INVENTION

One of the known functions of serum albumin is the binding and transport of various molecules in the blood circulation, including fatty acids, bilirubin, hormones, metal ions and other endogenous and exogenous compounds with widely differing properties (Murayama and Tomida, 2004). Among other substances, various drugs are known to bind to one of two main high affinity sites in albumin (Kragh-Hansen et al., 2002). It is also a very soluble protein, stable at pH ranging from 4 to 9 and at temperatures over 60° C., and available in high purity at a reasonable cost (Peters, 1977, 1985). These properties, and especially the natural affinity of a great number of therapeutic drugs to the protein, suggest that albumin may be used as a versatile carrier protein for various applications in the clinic. Some of the drug delivery technologies that make use of albumin as a drug carrier were recently reviewed by Kratz (2008).

There are several examples for the use of albumin in drug delivery systems, for example after incorporation of the albumin and the drug in a polymeric delivery system (Murray et al., 1983).

The covalent conjugation of Poly-(ethylene glycol) (PEG) to albumin, named PEGylation, was first described in 1977 (Abuchowski et al.) for purposes of reducing the immunogenicity of the protein. Other bioactive molecules, including various drugs, have also been PEGylated in order to prolong their residence time in the blood stream by improving their physical and thermal stability, increasing their protection against proteolysis and decreasing their clearance (Caliceti and Veronese, 2003; Greenwald et al., 2003).

PEGylated albumin hydrogels for drug delivery applications were previously described in the literature (Gayet and Fortier, 1995, 1996; Wacker et al., 2006; Iza et al., 1998). However, in these cases the release rate from the hydrogels was dominated by Fickian diffusion and not controlled by the specific affinity of the various drugs examined to albumin.

Hydrogels may be chemically designed to allow sustained release in response to environmental changes, such as temperature induced phase transition (Wang et al., 1999). Another way to control release kinetics of a drug from a hydrogel is by designing its swelling properties, based mainly on the synthetic polymer properties, including volume fraction, molecular weight between cross-linking points and the corresponding mesh size (Peppas et al., 2000). The degradation rate of the network may also be designed, based on the bioactive component, inducing controlled release of drug molecules (Huynh et al., 2008).

Tissue engineering, i.e., the generation of new living tissues in vitro, is widely used to replace diseased, traumatized or other unhealthy tissues. The classic tissue engineering approach utilizes living cells and a basic scaffold for cell culture. Thus, the scaffold structure attempts to mimic the natural structure of the tissue it is replacing and to provide a temporary functional support for the cells.

Tissue engineering scaffolds are fabricated from either biological materials or synthetic materials, such as polymers. Synthetic materials such as polyethylene glycol (PEG), hydroxyapatite/polycaprolactone (HA/PLC), polyglycolic acid (PGA), poly-L-lactic acid (PLLA), polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and polytetrafluoroethylene (PTFE) provide precise control over the mechanical properties of the material (Drury and Mooney, 2003).

Scaffolds made of PEG are highly biocompatible and exhibit versatile physical characteristics based on their weight percent, molecular chain length, and cross-linking density. In addition, PEG hydrogels are capable of a controlled liquid-to-solid transition (gelation) in the presence of cell suspension. Moreover, the PEG gelation (i.e., PEGylation) reaction can be carried out under non-toxic conditions in the presence of a photoinitiator or by mixing a two-part reactive solution of functionalized PEG and cross-linking constituents (Lutolf and Hubbell, 2003).

WO 1995/015352 describes a hydrogel comprising albumin and bifunctionalized polyethylene oxide. WO 2005/061018 describes a scaffold comprising a naturally occurring protein such as fibrinogen cross-linked by PEG, by attaching modified PEG molecules to cysteine residues of the protein. WO 2008/126092 describes a scaffold comprising albumin attached to at least two synthetic polymers.

A single PEG molecule conjugated to an albumin protein molecule through an amino group, as a model for assessing the abilities of a quantitative assay of PEG, is described by Nag et al, 1996.

SUMMARY OF THE INVENTION

The present invention relates to conjugates of albumin and a synthetic polymer for controlled delivery of therapeutic agents based on the therapeutic agent-albumin affinity.

In one aspect, the invention relates to a hydrogel system for controlled release delivery of a therapeutic agent, wherein said hydrogel comprises polymer-conjugated albumin molecules.

The polymer for use in the present invention is a functionalized derivative of a synthetic polymer selected from a polyalkylene glycol, preferably polyethylene glycol (PEG), hydroxyapatite/polycaprolactone (HA/PLC), polyglycolic acid (PGA), poly-L-lactic acid (PLLA), polymethyl methacrylate (PMMA), polyhydroxyalkanoate (PHA), poly-4-hydroxybutyrate (P4HB), polypropylene fumarate (PPF), or polytetrafluoroethylene (PTFE).

In certain embodiments, the synthetic polymer has two functional groups at the terminal ends, the first functional group being capable of attaching to the albumin and the second functional group being capable of attaching to the matrix. The first functional group (for attachment to the albumin molecule, preferably to a cysteine residue) may be selected from acrylate, aldehyde, tosyl, tresyl, dichlorotriazine, epoxide, succinimidyl succinate, succinimidyl ester, p-nitrophenyl carbonate, benzotriazolyl carbonate, 2,3,5-trichlorophenyl carbonate, succinimidyl carbonate, pyridyldisulfide, maleimide, vinylsulfone, and iodoacetamide.

In preferred embodiments, the first functional group is acrylate.

In certain embodiments, the first and the second functional groups of the functionalized polymer are identical to each other, and are both preferably acrylate.

In certain preferred embodiments, the synthetic polymer is polyethylene glycol (PEG) functionalized at the terminal ends by acrylate, and may be linear or branched PEG-diacrylate (PEG-DA), wherein the PEG has a molecular weight in the range of 0.4 kDa to 20 kDa, preferably 0.4 to 10 kDA.

The albumin in the polymer-conjugated albumin is preferably mono-substituted, and is more preferably substituted by PEG-DA (herein referred to as "mono-PEGylated albumin").

In certain preferred embodiments, each of the polymer-conjugated albumin molecules in the hydrogel system of the invention is linked to a matrix via a second functional group of the polymer.

The matrix may be composed of a polymer identical to the polymer of the polymer-conjugated albumin molecule, or may be different. In certain preferred embodiments, the matrix and the polymer of the polymer-conjugated albumin are the same and are preferably both PEG-DA.

The present invention further provides a hydrogel composition for sustained release of a therapeutic agent comprising a hydrogel system as described herein and the therapeutic agent, which may be bound to the albumin.

The therapeutic agent should have affinity to albumin in its natural form or it may be modified in order to acquire affinity to albumin. The therapeutic agent can be selected, without limitation, from a disinfectant, a chemotherapeutic agent, an antimicrobial agent, an antiviral agent, a hemostatic agent, an antiphlogistic agent, an anesthetic, an analgesic, a nutritional supplement, a hormone, a growth factor, a peptide, a polypeptide, a plasma derivative protein, a lipid or an enzyme.

Examples of therapeutic agents include, but are not limited to, pironolactone, Azapropazone, Digitoxin, Benzodiazepine, Glyburide, Tolbutamide, Chlorpropamide, Tenoxicam, Valproate, Piretanide, Quercetin, Oxyphenbutazone, Furosemide, Salicylate, Phenylbutazone, Acenocoumarol, Indomethacin, Iophenoxate, Iodipamide, Canrenoate, Diazepam, Ketoprofen, Chlofibrate, Iopanoate, Ibuprofen, Pirprofen, Ethacrynate, Diclofenac, Etodolac, Carprofen, Warfarin, Naproxen, Insulin, progesterone, testosterone, prostaglandin, thyroxine.

In certain embodiments, the hydrogel composition comprising a therapeutic agent may further comprise a bioactive polypeptide exhibiting tissue regeneration properties, thus allowing a combination of sustained release of the therapeutic agent and tissue regeneration. Examples of such bioactive polypeptides for tissue regeneration include fibrinogen, collagen, and the like.

The hydrogel composition may be in the form of an implant comprising the hydrogel system with a therapeutic agent.

The present invention further provides a method of generating the hydrogel system of the invention, the method comprising:

(a) covalently attaching albumin to a synthetic polymer through a first functional group of said synthetic polymer, said synthetic polymer having a second functional group, to thereby obtain a polymer-conjugated albumin precursor molecule;

(b) mixing the polymer-albumin precursor molecule of (a) with a synthetic polymer comprising a functional group capable of copolymerizing with said second functional group of said synthetic polymer of said precursor molecules.

(c) subjecting the mixture of (b) to copolymerization, to thereby generate said hydrogel system comprising a matrix to which a plurality of polymer-conjugated albumin molecules are linked via said second functional group of said synthetic polymer.

The synthetic polymer added in step (b) comprising a functional group capable of copolymerizing with the second functional group of the synthetic polymer of said precursor molecules may be the same or different from the synthetic polymer of the precursor molecules. In certain preferred embodiments, the two polymers are identical to each other and are, more preferably, PEG-DA.

In certain embodiments, a therapeutic agent is added to the mixture of (b) above, before copolymerization.

In certain embodiments, the copolymerization is initiated by ultraviolet illumination, optionally in the presence of a photoinitiator.

The invention further provides a hydrogel composition for sustained release of a therapeutic agent, said composition comprising: (i) a synthetic polymer-conjugated albumin; (ii) a synthetic polymer capable of copolymerization with the synthetic polymer of (i); (iii) a therapeutic agent; and (iv) a photoinitiator. The synthetic polymers of (i) and (ii) may be identical and are preferably are PEG-DA. This composition may be administered and subjected to photoillumination in vivo.

Thus, further provided is a method of administering a therapeutic agent in a sustained manner to a subject in need thereof, the method comprising administration of a hydrogel composition defined above to the subject, followed by local photoillumination.

BRIEF DESCRIPTION OF THE DRAWINGS

FIGS. 3A-3B show drug release experiments. (A) percent of drug released with time from hydrogels composed of PEG, PEGylated albumin, PEGylated fibrinogen, PEG with wild-type albumin, and mono-PEGylated albumin before and after purification. (B) log of drug released percent as a function of log of time for the same samples. The equation of each trend line is in the color of the related graph.

DETAILED DESCRIPTION OF THE INVENTION

Figure 1:
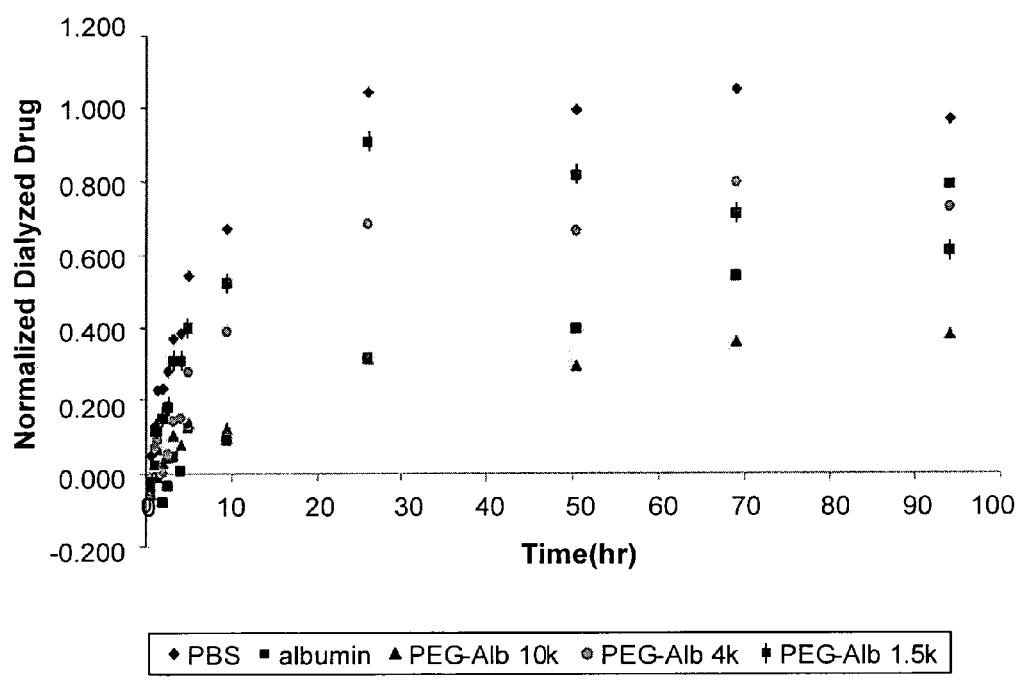
FIG. 1 shows results of dialysis equilibrium experiments. Percent of drug transferred through the dialysis membrane with time from solutions of PBS, wild-type albumin and PEGylated albumin (1.5, 4 and 10 kDa, results of a typical experiment). Insert: the percent of drug transferred through the dialysis membrane 24 hr after the experiment beginning from solutions of PBS, wild-type albumin and PEGylated albumin (1.5, 4 and 10 kDa).

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In a certain aspect, the present invention relates to a hydrogel system made from a polymer-conjugated albumin for affinity-based drug delivery, more particularly for controlled/sustained release of therapeutic agents.

In the hydrogel system of the present invention, also herein referred to as "hydrogel matrix", each of a plurality of albumin molecules covalently linked to a synthetic polymer having a free functional group, may be linked to a matrix via said free functional group of the polymer-albumin conjugate.

As a drug delivery vehicle, biodegradable albumin hydrogels can combine the high binding capacity of albumin with the structural stability of a polymeric hydrogel network to enable controlled release of small molecules based on both binding affinity and physical interactions. In accordance with the present invention, the development of a hybrid hydrogel composed of albumin conjugated to PEG for drug delivery applications is described, where controlled release is accomplished using the natural affinity of the drugs to the serum albumin.

As used herein, the term "matrix" encompasses solid substrates and semi-solid substrates (e.g., a gel), including solid particles and solid phases of colloids. The matrix may be any two-dimensional or a three-dimensional supporting framework.

The term "polymer" refers to a molecule composed primarily of a plurality of repeating units. The phrase "synthetic polymer" refers to any polymer which is made of a synthetic material, i.e., a non-natural, non-cellular material.

In some embodiments of the present invention, the matrix is comprised within a scaffold. As used herein, the term "scaffold" describes a supporting framework of a 3-dimensional structure. Optionally, the scaffold forms a hydrogel. For example, the scaffold may form a hydrogel when combined with an aqueous liquid, wherein the scaffold forms the solid phase of the hydrogel.

In some embodiments, the hydrogel system further comprises a therapeutic agent. Optionally, the therapeutic agent is bound to the albumin molecules. A plurality of therapeutic agents may be present.

Optionally, the synthetic polymer is suitable for implantation for sustained delivery of the drug. The polymer should be relatively non-harmful when implanted in a subject. Suitable synthetic polymers are known in the art and were described hereinabove.

In exemplary embodiments, the synthetic polymer is PEG of a. molecular weight in the range of 0.4 kDa to 20 kDa. The PEG molecule used by the present invention can be linear or branched (i.e., 2-arm, 4-arm, and 8-arm PEG) and can be of any molecular weight, e.g., 0.4 kDa, 1.5 kDa, 4 kDa, 6 kDa, 10 kDa and 20 kDa for linear PEG, 14 kDa and 20 kDa for 4-arm-star-PEG, and 14 kDa and 20 kDa for 8-arm-star-PEG and combinations thereof. It will be appreciated that branched synthetic polymer molecules are particularly suitable for linking more than one albumin molecule to the matrix.

For the sake of clarity, it is to be understood that the names of the abovementioned polymers as used throughout the application refer to the repeating units which make up the majority of the structure of the synthetic polymers, but the polymer for use in the present invention is in fact functionalized, preferably with two functional groups. Thus for example, the synthetic polymer consisting of polyethylene glycol with two acrylate groups (i.e., PEG-diacrylate) is encompassed herein by the terms "polyethylene glycol" and "PEG".

Exemplary functional groups capable of crosslinking include, without limitation, acrylate and vinyl sulfone.

As described herein, and exemplified in the Examples section below, the hydrogel systems described herein may be generated in a simple and convenient manner from albumin-polymer conjugates ("precursor molecules"). Furthermore, it is conveniently possible to adjust the biological and mechanical properties of the matrix by modifying, for example, the concentrations and species of precursor molecules, as described herein.

Hence, according to another aspect of the present invention, there is provided a method of generating a hydrogel system of the invention, the method comprising:

(a) covalently attaching albumin to a synthetic polymer through a first functional group of said synthetic polymer, said synthetic polymer having a second functional group, to thereby obtain a polymer-conjugated albumin precursor molecule;

(b) mixing the polymer-albumin precursor molecule of (a) with a synthetic polymer comprising a functional group capable of copolymerizing with said second functional group of the synthetic polymer of the precursor molecules.

(c) subjecting the mixture of (b) to copolymerization, to thereby generate said hydrogel system comprising a matrix to which a plurality of polymer-conjugated albumin molecules are linked via said second functional group of said synthetic polymer.

According to the present invention, the matrix may be formed concurrently with the linking of precursor molecules to the matrix, for example, by carrying out the method with an excess of the synthetic polymer, e.g. PEG-DA, as shown herein, said synthetic polymer in excess forming the matrix to which the precursor molecules are linked.

Thus, in an optional embodiment, the matrix is optionally formed by copolymerizing a plurality of polymer units capable of forming a matrix with a plurality of precursor molecules, thereby forming a matrix with precursor molecules linked thereto. The polymer units in this embodiment are preferably selected so as to be capable of copolymerizing with the second functional group of the precursor molecules.

The polymer units may be identical or different. The polymer units may undergo polymerization by linking to like polymer units. Alternatively or additionally, the polymer units may undergo polymerization by linking to different molecules (e.g., condensation of diacid and diamine).

In some embodiments, the first and second functional groups of the synthetic polymer are identical to the functional group on the polymer unit. In such an embodiment, the first functional group must be capable of attaching to the albumin, whereas the second functional group must be capable of linking to the (identical) functional group on a polymer unit. Thus, any functional group capable of both attaching to albumin and linking to like groups may be used as both the first functional group, second functional group, and polymer unit functional group. Exemplary groups include, without limitation, acrylate and vinyl sulfone. Thus, for example, the double bond of acrylate and vinyl sulfone may be attached to albumin (e.g., to a thiol group of the protein) by a Michael-like addition reaction, and may link the linker and polymer unit in the chain polymerization.

According to an optional embodiment of the present invention, the synthetic polymer comprises PEG comprising from 2 to 8 acrylate groups, wherein said 2 to 8 acrylate groups include the first and second functional groups described hereinabove.

Thus for example, linear PEG may be attached to albumin at one end, and be attached at the other end to the matrix, e.g., via an acrylate group (e.g., —OC(=O)—CH=CH$_2$)). 4-arm branched PEG may be attached, for example, at one end to an albumin molecule, and be attached at the other 3 ends to the matrix. Alternatively, 4-armed branched PEG may be attached to an albumin molecule at each of three ends (e.g., to three albumin molecules), and at one end to the matrix. Similarly, 8-armed branched PEG may be attached at one end to an albumin molecule, and be attached at the other 7 ends to the matrix (or vice versa).

Due to the ease of copolymerization of the precursor molecules with a polymer unit, as described herein, a matrix to which albumin is linked may be generated either inside (i.e., in vivo) or outside of a body. Copolymerization in vivo, for example, may be used to generate a matrix (e.g., a scaffold) having the exact shape of the cavity in the body that is to be filled with the matrix.

Various methods of linking the precursor molecules to a matrix are known in the art. For example, linking may be effected by illumination (e.g., by ultraviolet light), by chemical reagents (e.g., free radical donors) and/or heat.

According to an optional embodiment of the present invention, the linking (e.g., copolymerization of polymer units and precursor molecules) is by illumination with ultraviolet light (e.g., at a wavelength of about 365 nm).

As used herein the term "about" refers to ±10%.

When linking the synthetic polymer to the albumin and/or to the matrix in vivo, it is preferable to avoid doses of ultraviolet light that are harmful. The maximal dose which is non-harmful will depend, for example, on the wavelength of ultraviolet light used, and on the part of the body exposed to ultraviolet light. One skilled in the art will readily be capable of determining whether a dose is harmful or non-harmful.

Optionally, a photoinitiator is added to facilitate linking. Addition of a photoinitiator will typically enable one to use lower doses of ultraviolet light for linking.

As used herein, the term "photoinitiator" describes a compound which initiates a chemical reaction (e.g., a linking reaction, chain polymerization) when exposed to ultraviolet illumination. Many suitable photoinitiators will be known to one skilled in the art. Exemplary photoinitiators include, without limitation, bis(2,4,6-trimethylbenzoyl)phenylphosphine oxide (BAPO), 2,2-dimethoxy-2-phenylacetophenone (DMPA), camphorquinone (CQ), 1-phenyl-1,2-propanedione (PPD), the organometallic complex Cp'Pt(CH(3))(3) (Cp'=eta(5)-C(5)H(4)CH(3)), 2-hydroxy-1-[4-(hydroxyethoxy)phenyl]-2-methyl-1-propanone (e.g., Irgacure™ 2959), dimethylaminoethyl methacrylate (DMAEMA), 2,2-dimethoxy-2-phenylaceto-phenone, benzophenone (BP), and flavins.

According to an optional embodiment of the present invention, unconjugated synthetic polymer molecules (i.e., synthetic polymer molecules which failed to attach to the albumin) are removed from the precursor molecules prior to linking of the precursor molecules to the matrix.

Optionally, the unconjugated synthetic polymer (i.e., synthetic polymer that is not a component of a precursor molecule) is less than 20%, optionally less than 15%, optionally less than 10%, and optionally less than 5%, of the total weight of all the dry weight material (e.g., precursor molecules and unconjugated synthetic polymer) being linked to the matrix.

It is to be noted that one may remove unconjugated synthetic polymer prior to linking of the precursor molecules to the matrix, and then add the same unconjugated synthetic polymer as a polymer unit for copolymerization with precursor molecules. For example, it may be desirable to remove unconjugated synthetic polymer of which the concentration is uncertain, and then add unconjugated synthetic polymer at a known concentration.

For controlled release, the therapeutic agent is added to the hydrogel system of the invention. The therapeutic agent should be nonreactive with the hydrogel and may be included in the hydrogel, for example, by dissolving or suspending in the aqueous liquid comprised by the hydrogel. Methods of loading hydrogels with pharmaceuticals are well known in the art.

In preferred embodiments, the therapeutic agent is bound to the albumin of the precursor molecules when loaded onto the matrix.

According to an optional embodiment of the present invention, the matrix is biodegradable. According to another optional embodiment of the present invention, the albumin linked to the matrix is biodegradable.

As used herein, the terms "biodegradable" and "biodegradability" refer to being capable of being degraded (i.e., broken down) by biological proteases or other biomolecules. Biodegradability depends on the availability of degradation substrates (i.e., biological materials or portion thereof), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. In addition, biodegradability of a material, such as the matrix and/or the albumin-synthetic polymer conjugate of the present invention, also depends on the material structure and/or mechanical properties, i.e., the porosity, flexibility, viscosity, crosslink density, hydrophobicity/hydrophilicity, and elasticity which may affect passage and availability of gasses and nutrients, as well as cell attachment and spreading.

The biodegradability can be determined by selecting a biodegradable or non-biodegradable synthetic polymer. The biodegradability of a polymer may be determined, for example, by including a suitable proportion of biodegradable units in a polymer.

The biodegradability of a matrix (e.g., hydrogel scaffold) and/or albumin of embodiments of the present invention can be determined by subjecting the material to enzymatic degradation using proteases such as plasmin, trypsin, collagenase, chemotrypsin and the like.

Preferably, the hydrogel system of the present invention can be used for sustained release applications, as described herein. Optionally, the hydrogel system may comprise one or more other bioactive molecules, such as fibrinogen and/or collagen, for combined drug delivery and tissue regeneration and/or tissue repair applications.

The present inventors have uncovered, through laborious experimentations and screening novel conditions for generating albumin conjugates, that the hydrogel systems described herein are particularly suitable for releasing a compound (e.g., a therapeutic agent) in a controlled, sustained manner.

Hence, the present invention provides the use of a hydrogel system described herein for releasing a therapeutic agent in a sustained manner (e.g., in the manufacture of a medicament capable of a sustained release of a therapeutic agent).

In the context of such a use, the albumin-peptide conjugate may be linked to a matrix as described herein, wherein a therapeutic agent is further added. The therapeutic agent may be added after generating a matrix, or by adding the therapeutic agent to the polymer units and precursor molecules used to generate the matrix.

Alternatively, the hydrogel system may be prepared initially without a therapeutic agent, such that the therapeutic agent may be added at a later date.

As used herein, the term "sustained" refers to release with a half-life of at least one day. In some embodiments the half-life is at least 3 days, in some embodiments at least 7 days, in some embodiments at least 14 days, in some embodiments at least 30 days, in some embodiments at least 100 days, in some embodiments at least one year, and in some embodiments at least 500 days.

Sustained release of a therapeutic agent, may be used for example, to administer a therapeutic agent in a sustained manner to a subject in need thereof, by contacting the subject with a hydrogel composition described herein, the hydrogel composition including a therapeutic agent. The contacting may be done ex vivo (e.g., by contacting with the skin) or in vivo (e.g., by implantation in a suitable location in the body).

Sustained release may be performed, for example, using a drug delivering bandage, i.e. putting a thin slab of the matrix (e.g., a hydrogel) onto the skin, covered by a suitable plaster for prevention of movement and dehydration, and allowing sustained drug delivery from the matrix and through the skin.

The sustained release may be controlled by linking the albumin to the matrix in a suitable manner. Thus, albumin molecules linked to the matrix by a low number of synthetic polymer molecules (for example, 1 albumin: 1 polymer molecule, e.g., mono-PEGylated albumin) in general exhibit slower release of a bound compound (e.g., therapeutic agent).

Without being bound by any particular theory, it is believed that albumin has a natural affinity to a wide variety of compounds, but that attachment of multiple synthetic molecules to an albumin molecule reduces the affinity to the albumin molecule to compounds considerably, resulting in faster release.

However, under conditions wherein release of a compound is mediated considerably by degradation of the albumin (e.g., by proteases), an increased number of synthetic polymer molecules may shield the albumin from degradation, thereby slowing release.

In addition, the size (e.g., molecular weight) of the synthetic polymer may affect release. For example, a large polymer may more effectively reduce the affinity of albumin to a compound, resulting in faster release.

Thus, the rate of release of a therapeutic agent from the hydrogel system may be predetermined by one of ordinary skill in the art to suit a particular need.

Thus, as an exemplary example, bovine serum albumin was conjugated to PEG-diacrylate having a molecular weight of 1.5, 4 or 10 kDa to form a PEGylated albumin macromolecule (mono-PEGylated or multi-PEGylated). Biodegradable hydrogels were formed from the PEGylated albumin using photopolymerization. Two model drugs, Warfarin and Naproxen, were used for equilibrium dialysis and release experiments from the hydrogels, both having relatively low molecular weights and a known high affinity for albumin. Equilibrium dialysis experiments showed that multi-PEGylation of albumin decreases significantly the drug affinity to the protein compared to non-PEGylated controls, irrespective of the PEG molecular weight. However, the results from drug release experiments show that mono-PEGylation of albumin does not change its natural affinity to the drug, and comparing the release profiles with a Fickian diffusion model provides strong evidence that hydrogels containing mono-PEGylated albumin exhibit sub-diffusive drug release properties based on the affinity of the drug to the tethered protein. Biodegradation experiments substantiate the proteolytic breakdown of the albumin-based hydrogels, thus enabling their use as a general platform for sustained delivery of various drugs in vivo, with control over the release rate according to the molecular interaction between the drug, the polymer network and the albumin.

In accordance with the present invention, we describe the development of a novel mono-PEGylated albumin hydrogel system for drug delivery purposes, based on the natural affinity of various drugs to the albumin protein. It is known that PEGylation of proteins is often accompanied by loss of biological activity, although protein drugs PEGylation has many advantages, including shielding the protein surface from degrading agents by steric hindrance, increased size and solubility, and decreased kidney clearance (Veronese and Pasut, 2005). It is shown herein that the mono-PEGylation process allows us to maintain the affinity of drugs to albumin while conjugating the protein in a hydrogel matrix.

We have also used two drugs, Naproxen and insulin, to further characterize the drug release properties of the mono- PEGylated albumin hydrogels (10 kDa PEG-DA). Naproxen, a non-steroidal anti-inflammatory drug (NSAID), is one of the drugs that are known to bind with high affinity to multiple binding sites on serum albumin ($K_a$ of 1.6-3.7× $10^6$ $M^{-1}$) (Kragh-Hansen et al., 2002). We used Naproxen as a model drug for characterization of the drug release kinetics from the presented hydrogels due to this high binding affinity, as well as its relatively low molecular weight (230 Da). Naproxen is also a fluorescent molecule, allowing us to fluorescently measure the release kinetics of the drug molecules from the hydrogel, while avoiding any changes in its conformation or diffusion properties which may occur during labeling of such a low molecular weight molecule.

Two types of regular human insulin, ACTRAPID® and Insulin Detemir (LEVEMIR®), were also used herein for drug release characterization. While regular insulin (ACTRAPID®) has no binding affinity to serum albumin, Detemir is a regular insulin molecule which is modified by myristylation at B29 position to permit reversible insulin-albumin binding in the blood circulation. The non-covalent interactions of Detemir with albumin ($K_a$=1.0×$10^5$ $M^{-1}$) prevents rapid elimination of this type of insulin, since 98% of the Detemir molecules are albumin bound in the circulation.

The results showed that the release kinetics of drugs from the mono-PEGylated albumin hydrogels is affected both by the size of the drug molecules, i.e. their diffusion properties, and by the affinity of the drug to albumin. Although Naproxen has higher affinity to albumin, Insulin Detemir was released in a slower manner from the hydrogel, probably due to the big difference in molecular weight (230 Da and 5.9 kDa for Naproxen and insulin Detemir, respectively). It is interesting to note that the release kinetics of Naproxen, a low molecular weight drug with high affinity to albumin, and Actrapid, a high molecular weight drug with no affinity to albumin, are similar. This kind of experiments enables us to compare release kinetics of different drugs from the same hydrogel, and predict their relative in vivo release properties.

Figure 6A:
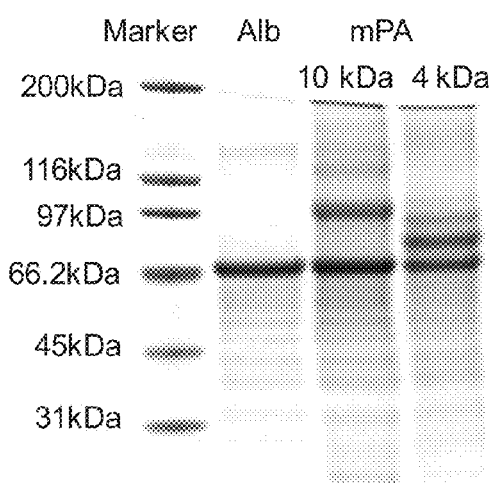
FIGS. 6A-6B show Naproxen release results. (A) typical SDS-PAGE results comparing un-reacted albumin with 10 kDa and 4 kDa mono-PEGylated albumin. (B) normalized amount of the drug Naproxen released with time from purified 10 kDa mono-PEGylated albumin hydrogels and from un-purified 4 kDa and 10 kDa mono-PEGylated albumin hydrogels. Average Naproxen release (last 30 min) was 0.55±0.04 for 4 kDa of PEG (not purified), 0.66±0.07 for 10 kDa of PEG (purified) and 0.78±0.07 for 10 kDa of PEG (not purified).

Using 4 kDa PEG-DA, we were able to produce a precursor solution containing unreacted albumin with albumin conjugated to one, two and three PEG molecules, as well as multi-PEGylated protein molecules. By improving our separation methods, this may open new possibilities of controlling the release characteristics from the hydrogels. It is important to note that the mono-, di- or tri-PEGylated albumin species does not appear in the SDS-PAGE gel exactly according to their molecular weight as would be expected according to the marker line, but in a higher molecular weight level (FIG. 6A). This may be a result of the extended conformation and high hydrodynamic molecular volume of PEG relative to proteins. However, when comparing the molecular weights of 10 kDa mono-PEGylated albumin and 4 kDa mono-, di- or tri-PEGylated albumin, the marks appear in the expected placements relative to one another. The SDS-PAGE results also indicate that the mono-PEGylation reaction, assumingly occurring with the Cys-34 residue, has a relatively low efficiency regardless of the PEG molecular weight. This may be explained by the location of the Cys-34 residue in a crevice on the surface of the albumin protein, which restricts its availability to reaction. It is also known that 30-50% of the albumin molecules in isolated albumin samples have Cys-34 blocked as a disulfide (Christodoulou et al., 1995).

Results of release experiments showed that 4 kDa mono-PEGylated albumin hydrogels produced a more sustained release in comparison to 10 kDa samples, although the majority of PEG molecules in the hydrogel matrix are free 10 kDa PEG-DA added to the albumin in both cases (6.5%). Hence, this is another prove to our assumption that the affinity of the drugs to the albumin molecule, which is affected in this case by PEG conjugation to albumin, is the dominant factor in respect of the drug release kinetics, and not the matrix density. The differences between release kinetics from the 10 kDa and 4 kDa PEGylated albumin hydrogels may be explained by greater steric hindrance and higher hydrated molecular volume as the PEG molecular weight is increased. The conjugated PEG molecule reduces the ability of the drug to approach its affinity sites on the protein. As the PEG molecular weight is reduced, the affinity of the drug to the conjugated protein is increased due to the lower steric repulsion, resulting in slower release kinetics from the hydrogel.

The effect of enzymatic degradation on the release properties of the hydrogels were examined for two main purposes: to compare the release rate in the experiments presented so far to the rate in the presence of a degrading enzyme, and to assess the function of similar hydrogels for drug delivery during tissue regeneration. In vivo, albumin is degraded mostly in lysosomes. Its degradation is in general slower than the degradation rate of fibrinogen (Peters, 1985). In our previous work (Gonen-Wadmany et al., 2007) we have shown that this is also true when these proteins are multi-PEGylated and crosslinked in the form of hydrogels. Here, we wanted to examine the effect of degradation on the release kinetics of drugs from mono-PEGylated albumin hydrogels. As expected, the results indicated that the drug is released faster in the presence of a degrading enzyme as a result of the degradation of the albumin protein, which decreases the affinity of the drug to the hydrogel. The protein is also a part of the hydrogel matrix, thus allowing faster diffusion into solution as the matrix is degraded. Without the enzyme, since most of the albumin is conjugated to the matrix, the protein is released more slowly out of the matrix and thus sustains the release of the drug, as also described herein. It is important to note that most of the albumin in the hydrogel is covalently conjugated to the matrix by mono-PEGylation, although complete purification is not achieved. Thus, there is also a small amount of unconjugated albumin trapped in the matrix by physical means only. This may explain the release of a relatively small amount of albumin from the matrix even without the presence of a degrading enzyme.

The results herein also indicate on the ability to achieve the same release kinetics from a hydrogel containing mono-PEGylated albumin with 6.5% free PEG-DA, and from a hydrogel containing mono-PEGylated albumin with PEGylated fibrinogen and 5% free PEG-DA. This enables us to design a hydrogel with the desired combination of controlled release properties and tissue regeneration properties. Furthermore, we may control the release rate of drugs from the hydrogel matrix by using different free PEG-DA additions, due to the polymer's effect on the degradation rate and the cross-linking density of the matrix.

The biofunctionality of the combined hydrogels was examined using three dimensional cell culture experiments. As shown in previous works published in our lab (Dikiwsky et al., 2006; Gonen-Wadmany et al., 2007), various cell types are able to spread and form networks in PEGylated fibrinogen hydrogels, due to the cell adhesion and proteolytic degradation sites of this protein. However, experiments done with multi-PEGylated albumin have shown no cell spreading, since albumin lacks any cell adhesion sites (Gonen-Wadmany et al., 2007). We show herein that this is also the case when mono-PEGylated albumin hydrogels are used. However, combined hydrogels containing 8 mg/ml mono-PEGylated albumin and 8 mg/ml fibrinogen enable cells spreading and the formation of networks, in spite of the relatively high total protein concentration (16 mg/ml). A lower fibrinogen concentration (4 mg/ml) in a combined hydrogel does not produce such good results, even though the total protein concentration is 8 mg/ml. These results indicate that the main factor affecting the cells spreading is the fibrinogen concentration and not the total protein concentration. Furthermore, the presence of albumin does not disturb the biofunctionality of fibrinogen in the hydrogel matrix.

As used herein, the term "subject" refers to a vertebrate, preferably a mammal, more preferably a human being (male or female) at any age.

The present invention provides also implants which can be implanted in the subject using a surgical tool such as a scalpel, spoon, spatula, or other surgical device.

The hydrogel system of the present invention can be also used for ex vivo formation of an implant. As used herein, the phrase "ex vivo" refers to outside of the living organism, preferably, outside the body of a vertebrate, a mammal, or human being.

The pharmaceutical/hydrogel compositions (medicaments) according to embodiments of the present invention may optionally be presented in a pack or dispenser device, such as an FDA-approved kit, which may contain one or more unit dosage forms (e.g., 100 mg) such as for personalized use containing the active ingredient (e.g., precursor molecules which are not yet crosslinked) and optionally sterile disposable means for delivery (e.g., syringe) and for illumination (e.g., illuminator covers). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

As used herein, the terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention Reference is now made to the following examples, which together with the above descriptions illustrate some embodiments of the invention in a non-limiting fashion.

EXAMPLES

Materials and Methods (i) PEG-Diacrylate Synthesis

PEG-diacrylate (PEG-DA) was prepared from linear PEG-OH MW=10 kDa, 4 kDa and 1.5 kDa (Fluka, Buchs, Switzerland) as described elsewhere [Almany and Seliktar, 2005, Biomaterials 26, 2467-2477]. In brief, acrylation of PEG-OH was carried out under Argon by reacting a dichloromethane solution of PEG-OH (Aldrich, Sleeze, Germany)

with acryloyl chloride (Merck, Darmstadt, Germany) and triethylamine (Fluka) at a molar ratio of 1.5:1 relative to —OH groups. The final product was precipitated in ice-cold diethyl ether and dried under vacuum for 48 hours. Proton NMR ($^1$HNMR) was used to validate end-group conversion and to verify purity of the final product (data not shown).

(ii) Albumin and Fibrinogen PEGylation

The PEGylation of fibrinogen and albumin was done according to PEGylation protocol similar to those described by Dikovsky et al. [Dikovsky et al., 2006], Tris (2-carboxyethyl) phosphine hydrochloride (TCEP HCl) (Sigma-Aldrich) was added to a 7 mg/ml solution of bovine fibrinogen (Sigma-Aldrich) or bovine serum albumin (MP Biomedicals, Ohio, U.S.A.) in 150 mM phosphate buffer saline (PBS) with 8 M urea (molar ratio 1.5:1 or 2:1 TCEP to fibrinogen or albumin cysteins, respectively). Linear PEG-DA (MW=10 kDa for fibrinogen, MW=10 kDa, 4 kDa and 1.5 kDa for albumin) was reacted for 3 hrs with the protein at a 4:1 or 2:1 molar ratio of PEG to fibrinogen or albumin cysteines, respectively.

29 or 35 cysteines were considered for a fibrinogen or albumin molecule, respectively. The PEGylation efficiency was ~85% for fibrinogen, and ~100%, ~75% and ~65% for 10 kDa, 4 kDa and 1.5 kDa PEGylation of albumin, respectively.

Mono-PEGylation of albumin was conducted in a similar way by adding a solution of linear PEG-DA (MW=10 kDa or Mw=4 kDa, 1:1 molar ratio of PEG to albumin cysteines) to a 7 mg/ml solution of bovine serum albumin (MP Biomedicals, Ohio, USA) in 150 mM phosphate buffer saline (PBS) with 8 M urea, and allowed to react at room temperature for up to 30 min, or overnight, for 10 kDa or 4 kDa PEGylation, respectively. The PEGylated protein products were precipitated in acetone and redissolved in PBS containing 8 M urea. The final protein concentration was 7 mg/ml for PEG-fibrinogen and 2-5 mg/ml for PEG-albumin. The protein products were dialyzed against PBS at 4° C. for 2 days (Spectrum, 12-14-kDa MW cutoff, California, U.S.A.). The 10 kDa PEGylated albumin was concentrated to 8 mg/ml by lyophilization and reconstitution. The PEGylation efficiency was ~20% before purification, when considering 35 cysteins per albumin molecule. The PEGylated products were characterized according to published protocols [Dikovsky et al., 2006; Gonen-Wadmany et al., 2007].

(iii) Fluorescence and Albumin Binding

To measure the binding affinity of albumin to the drug Warfarin, the fluorescence intensity of the drug was measured in the presence of either wild-type albumin or PEGylated albumin in PBS, and compared to its fluorescence in control solution (PBS, pH 7.4). Albumin binding was likewise quantified by reacting Warfarin in a 5 mg/ml solution of wild-type albumin or PEGylated albumin (10, 4 or 1.5 kDa PEG-DA) at a 10:1 molar ratio of albumin to Warfarin. The mixture was incubated for ~5 hours before reading fluorescence emission ($\lambda$=385 nm) at a 320 nm excitation wavelength using a Varioscan spectral scanning multimode reader (Thermo Electron Corporation, Vantaa, Finland).

(iv) Equilibrium Dialysis Experiments

To characterize the interactions between wild-type albumin or PEGylated albumin and Warfarin, we used an equilibrium dialysis method whereby a solution of albumin and drug were placed in a custom made dual-chamber device. The two chambers of the device were separated by a dialysis membrane (12-14 kDa MW cutoff) and drug diffusion was measured by fluorescence spectroscopy. One dialysis chamber of the device was filled with 25 ml PBS solution containing 0.1% (w/v) of sodium azide (Fluka). The other chamber was loaded with albumin samples and a known quantity of a 47 mM stock solution of Warfarin (A2250, Sigma) dissolved in DMSO, and incubated at room temperature. For characterizing the binding affinity of Warfarin to PEGylated albumin, 3.88 ml of PEG-albumin solution (1.5, 4 or 10 kDa PEG) was mixed with 0.12 ml of Warfarin stock solution, to give an albumin to Warfarin molar ratio of 5:1. Control samples of wild-type albumin in PBS were also tested using the same Warfarin molar ratios. Warfarin fluorescence emission intensity, which was correlated to its concentration, was recorded periodically from samples in the dialysate chamber using a Varioscan reader (Thermo Electron). Comparing the equilibrium concentrations following albumin-drug incubations was done after normalizing the fluorescence data with the equilibrium Warfarin diffusion results from a control PBS solution.

(v) Mono-PEGylated Albumin Purification by Gel Filtration

Gel filtration (or size exclusion chromatography) was used to purify the mono-PEGylated albumin species from the mixture of wild-type, mono-PEGylated and multi-PEGylated mixture produced during the <30 min reaction of albumin to PEG-DA. SEPHACRYL™ S-300 High Resolution prepacked gel filtration columns (Amersham Biosciences, Uppsala, Sweden) were used in a BIOLOGIC DUOFLOW™ Chromatography system (Bio-Rad Laboratories, California, U.S.A.). Samples were run against a buffer of 0.02 M Tris-HCl with a flow rate of 1.6 ml/min and detection at $\lambda$=280 nm. Purified fractions of mono-PEGylated albumin were collected and characterized by gel electrophoresis (SDS-PAGE). These fractions were merged and concentrated to ~10 mg/ml by lyophilization and reconstitution, and then dialyzed against PBS at 4° C. for 2 days.

For producing a precursor solution containing both PEGylated fibrinogen and purified 10 kDa mono-PEGylated albumin, the reconstitution was done by dissolving the lyophilized PEGylated protein with a PEGylated fibrinogen solution. The final concentrations of both albumin and fibrinogen in the solution were adjusted to 8 mg/ml.

(vi) SDS-PAGE

The wild-type albumin and the PEGylated albumin, including the chromatography fractions, were characterized by SDS-PAGE whereby PEGylated and unPEGylated proteins were loaded into CRITERION™ XT precast 10% or 4-12% gradient Bis-Tris gels (5-10 µg of solution in each lane, Bio-Rad). The gels were stained with COOMASSIE® blue and digitally imaged using a gel documentation workstation.

(vii) Drug Release Experiments

The kinetics of drug release from hydrogels was tested using as models the drugs Naproxen (Fluka) and the insulin formulations LEVEMIR® and ACTRAPID® (100 IU/ml, Novo Nordisk A/S, Bagvaerd, Denmark). A stock solution of 0.1 mg/ml Naproxen in PBS with 0.1% (w/v) of sodium azide was prepared. Both LEVEMIR® and ACTRAPID® were fluorescently labelled by 5 mg/ml NHS-fluorescein (Pierce, Illinois, U.S.A.) in DMSO, with a molar ratio of 15:1 NHS-fluorescein to insulin. The solution was allowed to react for 5 hr in 4° C. and dialysed (Cellu-Sep H1, 1-kDaMW cutoff, Texas, U.S.A.) against PBS with 0.1% (w/v) of sodium azide with DMSO in decreasing concentrations of DMSO (10-0%) for 1 week.

The drug was added to the PEGylated protein precursor solution in a molar ratio of 5:1 or 10:1 albumin to Naproxen or insulin, respectively. The drug was saturated in disk-shaped hydrogel constructs prepared from PEG-DA or PEGylated proteins, that were formed into hydrogels by photopolymerization using 0.1% (w/v) Irgacure™ 2959

(Ciba Specialty Chemicals, Basel, Switzerland) and UV light (λ=365 nm, 4-5 mW/cm$^2$) exposure for 5 min as described elsewhere (Gonen-Wadmany et al., 2007). The hydrogel constructs were produced from six different hydrogel precursor solutions, including: (i) purified mono-PEGylated albumin in PEG-DA; (ii) non-purified mono-PEGylated albumin (containing wild-type and multi-PEGylated albumin) in PEG-DA; (iii) multi-PEGylated albumin in PEG-DA; (iv) wild-type albumin in PEG-DA; (v) PEG-DA; (vi) PEGylated fibrinogen in PEG-DA. In all cases, the protein (albumin or fibrinogen) concentration was 8.5 mg/ml, and the PEG-DA was added to reach a total PEG concentration of 7%. A stock solution of 0.1 mg/ml Naproxen was prepared and added to the precursor solution prior to photopolymerization at a molar ratio of 5:1, albumin to Naproxen.

Drug release from the hydrogel constructs into the supernatant was measured fluorescently (excitation at λ=330 nm and emission at λ=360 nm) in PBS with 0.1% (w/v) of sodium azide under constant agitation at 37° C. using a Varioscan plate-reader (Thermo Electron Corporation, Finland). (In the case of degradation experiments, 0.01 mg/ml of Trypsin (MP Biomedicals) was added to the PBS solution.) The raw data was normalized by the fluorescence intensity measured after 24 hours. The constructs were liquefied by homogenization or sonication (for multi-PEGylated albumin and fibrinogen), or by chemical means using 0.1 M NaOH, and the drug content was quantified to confirm complete drug release.

(viii) Diffusion Model Fitting

The drug release profiles were compared with a known model of diffusion-based release kinetics. One dimensional Fick's law of diffusion can be solved to give Equation 1 under the following assumptions: (i) the diffusion coefficient is independent of drug concentration; (ii) there is an infinite open system (i.e. the solution volume is greater than 20 times the volume of the hydrogel); (iii) A short release time (i.e. the amount of drug released is smaller than 60% of the amount released after long times).

$$\frac{M_t}{M_\infty} = kt^n \quad \text{Eq. 1}$$

Equation 1 predicts that $M_t$, the amount of drug released at time t, normalized by the amount of drug release after long times, $M_\infty$, follows a power law with time. The coefficients k and n are constants in this equation. In a diffusion controlled system, n=0.5 [Narasimhan et al., E. Mathiowitz (Ed), *Encyclopedia of Controlled Drug Delivery*, Vol. 2, John Wiley & Sons, Inc., New York, 1999, pp. 921-935]. For comparison of the release curves obtained in the experiments described above with this model, we used the log of the release data and used a linear regression, for times shorter than the time to reach 60% release (i.e. $M_t/M_\infty < 0.6$). The slope of the trend line, n was expected to be 0.5 in the case of diffusion based release; for n<0.5 the release is considered sub-diffusive, and for n>0.5 the release is considered super-diffusive.

(ix) Albumin Release Experiments

Albumin release experiments were performed similarly to the drug release experiments for both wild-type albumin and purified mono-PEGylated albumin mixed in with PEG-DA and polymerized into hydrogels. In the case of degradation experiments, albumin was fluorescently labelled by 7.5 mg/ml NHS-Fluorescein in DMSO, with a molar ratio of 2:1 NHS-Fluorescein to insulin. The solution was allowed to react for 5 hr in 4° C. and dialysed (Spectrum, 12-14 kDa MW cutoff) against PBS with 0.1% (w/v) of sodium azide with DMSO in decreasing concentrations of DMSO (2-0%) for 2 days. Albumin release from the hydrogel constructs into the supernatant was measured fluorescently (excitation at λ=491 nm and emission at λ=518 nm). In the case of release experiments without Trypsin, non-labelled albumin release was measured as described herein. Briefly, 100 μl samples of supernatant from the hydrogel incubation medium were analyzed for total protein by enhanced BCA™ protocol (BCA™ Protein Assay Kit, Thermo Scientific, Illinois, U.S.A.). The same volume of PBS was always returned to the supernatant. The plugs were degraded by 1 M NaOH after 24 hours, the protein concentration was determined, and the release results were normalized to the total albumin concentration of the degraded plugs.

(x) Statistical Analysis

Statistical analysis was performed using MICROSOFT® Excel software. Data from independent experiments were quantified and analyzed for each variable. Comparisons between multiple treatments were made with analysis of variance (ANOVA). A p-value of <0.05 was considered to be statistically significant.

(xi) 3-D Cell Culture Constructs

Cellularized constructs were made by photopolymerizing PEGylated protein precursor solution in the presence of dispersed human foreskin fibroblasts (HFFs). The passaged cells (P8) were trypsinized and suspended in 500 μl of PEGylated protein precursor (2×10$^6$ cells/ml) containing photoinitiator (0.1% w/v). Four types of precursor solutions were used, including: PEGylated fibrinogen (8 mg/ml protein concentration); un-purified 10 kDa mono-PEGylated albumin (8 mg/ml protein concentration, addition of 2% PEG-DA); PEGylated fibrinogen and mono-PEGylated albumin (8 mg/ml protein concentration for each protein); and PEGylated fibrinogen and mono-PEGylated albumin (4 mg/ml protein concentration for each protein, addition of 0.5% PEG-DA). The PEGylated fibrinogen and albumin samples were prepared by lyophilization of un-purified 10 kDa mono-PEGylated albumin, which was redissolved with PEGylated fibrinogen precursor solution to reach an equal protein concentration for albumin and fibrinogen. The desired total protein concentration was reached by addition of PBS.

To form a 3-D construct, 100 μl of a desired solution was photo-crosslinked by UV light exposure for 5 min in cylindrical molds. The encapsulated cells in the cylindrical constructs were kept in an appropriate medium, and were monitored and documented every other day using a phase contrast microscope. Cell morphology was also assessed by H&E staining of cross-sections of cellularized constructs a week after the beginning of the experiment.

Example 1

Mono-PEGylated Albumin-Based Precursor Molecules

Bovine serum albumin (MP Biomedicals, Ohio, U.S.A.) was dissolved in 150 mM PBS with 8M urea to give a 7 mg/ml solution. After dissolution, a solution of PEG-DA (280 mg/ml) in 150 mM PBS with 8 M urea was added. The molar ratio of PEG to albumin cysteins was 1:1 (linear PEG-DA, 10 kDa), i.e. 35:1 molar ratio to the single unconjugated cystein in albumin. After ~1 min of incubation the PEGylated protein was diluted with an equal volume of 150 mM PBS containing 8 M urea and precipitated by adding 5 volumes of acetone. The precipitate was redissolved using a homogenizer at ~10 mg/ml protein concentration in PBS containing 8 M urea and dialyzed against 150 mM PBS at 4° C. for 2 d with two changes of PBS. The produced solution contains a mixture of unPEGylated, mono-PEGylated and multi-PEGylated albumin. Isolation of the mono-PEGylated species was done using size exclusion chromatography. The mixture has been chromatographed on a SEPHACRYL® S-300 gel filtration column. Samples were eluted with 20 mM Tris-HCl buffer, pH 7.4, at a flow rate of 1.6 ml/min and 1 ml fractions were collected. After repeating this process for several times, fractions of different batches containing mainly the mono-PEGylated albumin species were united and lyophilized for at least 2 days. Following the lyophilization, the mono-PEGylated protein was redissolved in 150 mM PBS to reach a protein concentration of ~10 mg/ml.

Example 2

Multi-PEGylated Albumin-Based Precursor Molecules

Bovine serum albumin (MP Biomedicals, Ohio, U.S.A.) was dissolved in 150 mM PBS with 8 M urea to give a 7 mg/ml solution. TCEP HCl was added to the albumin solution (molar ratio 2:1 TCEP to albumin cysteins). After dissolution, a solution of PEG-DA (280 mg/ml) in 150 mM PBS with 8 M urea was added and reacted for 3 hours at room temperature. The molar ratio of PEG to albumin cysteins was 2:1 (linear PEG-DA, 10 kDa). After the incubation the PEGylated protein was diluted with an equal volume of 150 mM PBS containing 8 M urea and precipitated by adding 5 volumes of acetone. The precipitate was redissolved using a homogenizer at ~2 mg/ml protein concentration in PBS containing 8 M urea and dialyzed against 150 mM PBS at 4° C. for 2 days with two changes of PBS. Next, the PEGylated albumin solution was lyophilized for at least 2 days and redissolved in 150 mM PBS to reach a protein concentration of ~8 mg/ml.

Example 3

PEGylated Albumin Hydrogel Formation

PEGylated protein precursor solutions were formed into hydrogels by photopolymerization using 0.1% (w/v) Irgacure™ 2959 (Ciba Specialty Chemicals, Basel, Switzerland) and UV light (365 nm, 4-5 mW/cm$^2$) exposure for 5 min. Prior to UV light exposure, functionalized PEG molecules may be supplemented to the precursor solution for controlling the mechanical properties of the formed gel.

Example 4

PEGylation Affects Albumin-Warfarin Affinity

Our initial feasibility work with these hydrogels included equilibrium dialysis experiments and increased fluorescence experiments with the drug Warfarin. The binding of Warfarin molecules to serum albumin has been studied widely due to the strong affinity of this drug to albumin and the affect of this affinity on the bioavailability of the drug in the body. It has been known that Warfarin fluoresces with peak intensity at 385 nm with a 320 nm excitation. When Warfarin binds to its high affinity binding site on human serum albumin (HSA), its fluorescence is enhanced up to 10-fold over the fluorescence of unbound Warfarin. This effect has been widely used to determine the dissociation constant for the protein-drug interactions [18, 30, 31]. We used this known property of Warfarin herein to examine the influence of PEGylation on the affinity between the drug and albumin. We compared the fluorescence of a Warfarin solution to the fluorescence of a solution containing Warfarin and albumin, either unconjugated or PEGylated by 10, 4, and 1.5 kDa PEG-DA. The results (Table 1) show that there was a significant decrease of more than 40% in the affinity of the drug to PEGylated albumin in comparison to unreacted protein. However, there were no significant differences between the binding affinities of the drug to PEGylated albumin having different molecular weights of PEG-DA. It should be noted that unlike a 10-fold increase in fluorescence reported in the literature, we observed only a 2.8-fold increase when Warfarin was bound to wild-type albumin. A possible reason for this may be that the source of the albumin was bovine and not human.

Regardless of the albumin source, the results showed a significant decrease in the ability of the drug to bind to the albumin after its PEGylation. Albumin has two main binding sites; both are formed as pockets in the tertiary structure of the protein. Albumin's native structure is also based on a series of nine disulfide bonded loops. During the multi-PEGylation process, this tertiary structure is likely damaged in two ways: the three-dimensional natural folds are opened, and the disulfide bonds are reduced. These steps are followed by the chemical addition reaction of the polymer's diacrylate functional groups with the free cysteine residues of the protein. Thus, the tertiary structure of the protein is most certainly changed irreversibly, and its binding sites are significantly altered.

TABLE 1

Ratio between Warfarin fluorescence intensity and its intensity in the presence of wild-type or PEGylated albumin (1.5, 4 and 10 kDa). Fluorescence Intensity Ratio Comparing to Warfarin Alone (n = 6)

| Albumin | PEG-Alb 10 kDa | PEG-Alb 4 kDa | PEG-Alb 1.5 kDa |
| --- | --- | --- | --- |
| 2.8 ± 0.2 | 1.5 ± 0.5 | 1.5 ± 0.4 | 1.6 ± 0.3 |

Further examination of the albumin-Warfarin affinity after PEGylation was conducted using equilibrium dialysis experiments in order to see if the MW of the PEG-DA had an impact on the drug binding properties (FIG. 1). The graph in FIG. 1 shows the typical experimental results of the Warfarin transport kinetics from the drug/protein chamber into the dialysate chamber. These results indicate that the equilibrium state was achieved after about 24 hr. For wild-type albumin, some increase in the fluorescence was shown after more than 24 hr, possibly due to albumin molecules leaking through the dialysis membrane after very long incubation periods, and not because of continued drug molecule transport. A comparison of the equilibrium state is shown in the insert of FIG. 1. The percent of drug transported from the solution containing unreacted albumin was the lowest, indicating the highest affinity of the drug to the wild-type protein. In contrast, PEGylated albumin solutions allowed more drug molecules to diffuse through the membrane, indicating a lower affinity to the modified albumin. Another trend observed in these results was the lower affinity between the drug and the PEGylated albumin as the PEG molecular weight decreases: 4 kDa and 1.5 kDa PEGylated albumin species showed significantly less affinity to the drug, in comparison to wild-type albumin and 10 kDa PEGylated albumin. This trend was not observed in the fluorescence measurements described above (Table 1).

Example 5

Mono-PEGylation of Albumin

As a result of our understanding that the affinity of drugs to albumin was significantly lowered by the multi-PEGylation process, we examined whether a mono-PEGylation process also had similar effects. In the past, there have been attempts to conjugate a single PEG molecule to an albumin protein molecule through an amino group, for a demonstration of the abilities of a quantitative assay for PEG detection [33]. The mono-PEGylation of albumin performed in our lab, however, was targeted for one cysteine residue on the albumin molecule, $Cys^{34}$, which is the only cysteine residue out of 35 in the protein that is not involved in stabilizing disulfide bonds. This cysteine residue is theoretically available for reaction. We obtained mono-PEGylated albumin by reacting PEG-DA to the $Cys^{34}$ without reduction of disulfide bonds, under the assumption that some of the $Cys^{34}$ residues will be free for the addition reaction under these conditions. We were able to produce mono-PEGylated albumin following this reaction, as seen by SDS-PAGE (FIG. 2B, lane marked as "Mono-PEGylated Albumin"). Characterization of the end-product of this reaction showed the presence of unreacted and multi-PEGylated albumin, seen below 66 kDa and trapped in the loading portion of the gel, respectively. Multi-PEGylation of the albumin most likely occurred due to the reaction of the polymer's functional groups with amines on the protein, or with cysteine residues exposed by some protein denaturation during the reaction. On the other hand, some of the albumin molecules did not react with the PEG-DA because their $Cys^{34}$ residue was occupied by protein-protein disulfide bonds or they were in an oxidized state; this occurs in about 30-50% of the cysteine residues in isolated commercial albumin samples. Also, it has been found that this cysteine residue is not at the surface of the protein and may be accessible only to small molecules. The pH of the environment also affects the reactivity of this cysteine residue, due to changes in ionization of this group.

Figure 2A:
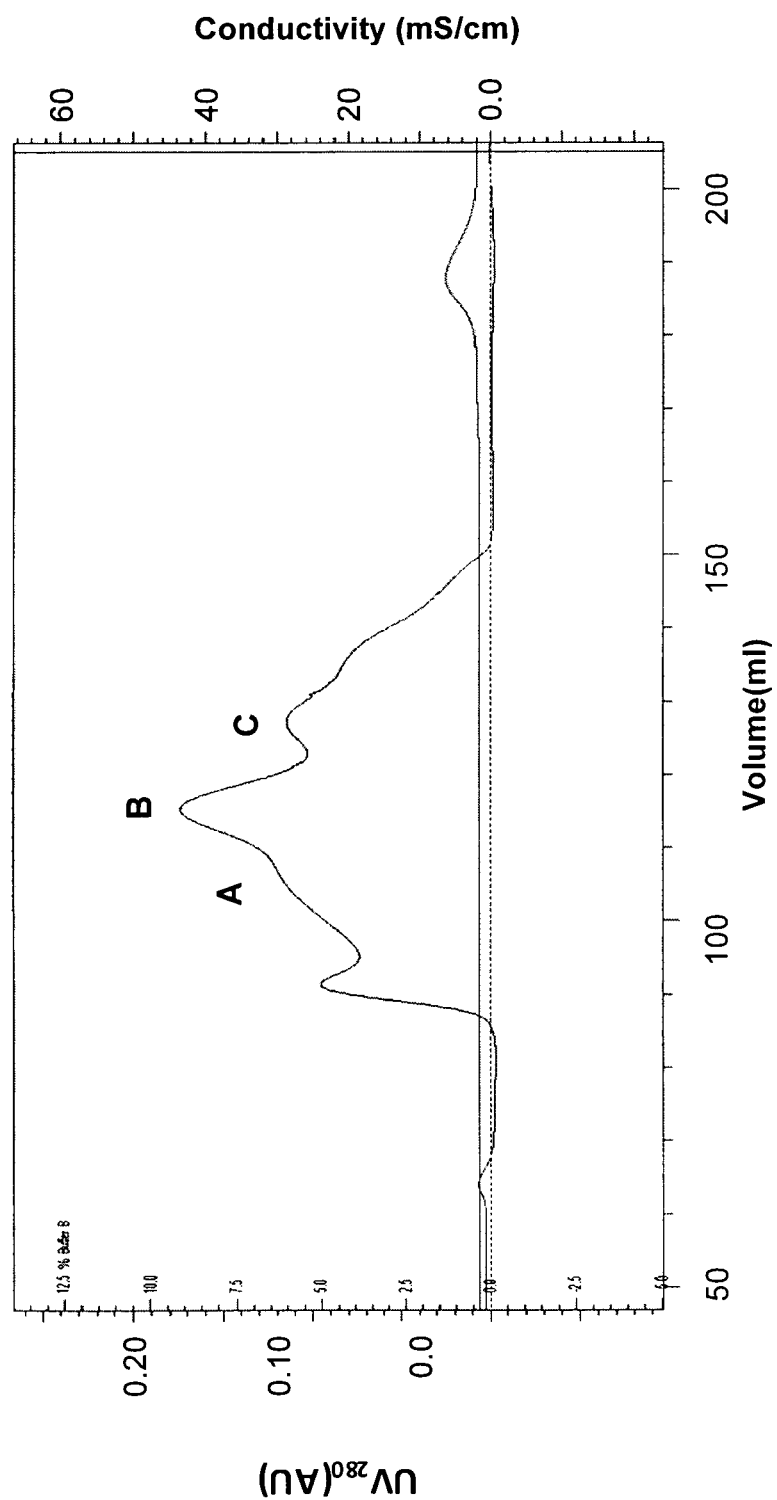
FIGS. 2A-2B show purification of mono-PEGylated albumin. (A) typical mono-PEGylated albumin gel filtration results: UV intensity (measured at 280 nm) and conductivity as a function of volume running through the gel filtration column. A, B and C mark the samples collected for further characterization. (B) typical SDS-PAGE results of collected samples, compared to mono-PEGylated albumin prior to gel filtration and to wild-type albumin.
Figure 2B:
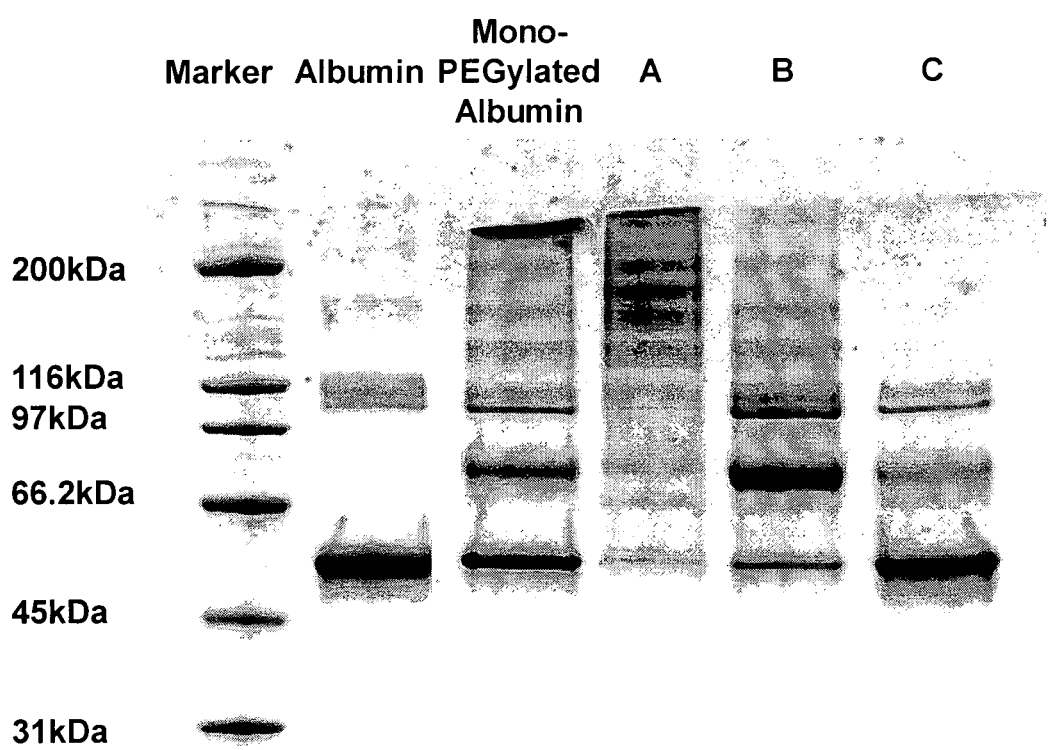

Purification of the mono-PEGylated albumin species from this mixture was achieved by gel filtration, using a size exclusion chromatography column, as shown in FIG. 2A. Characterization of the three main peaks in the chromatography results was done using SDS-PAGE (FIG. 2B). The results showed a separation between the three main species, thus allowing collection of three fractions, one of which contained mainly mono-PEGylated albumin (FIG. 2B, lane marked as "B"). These purified fractions were collected, amalgamated and concentrated for immobilization into the hydrogel constructs. Thus, the mono-PEGylation method enabled us to conjugate albumin to the hydrogel molecular network without harming the disulfide bonds or the wild-type conformation.

Example 6

Drug Release Experiments with Naproxen

For drug release experiments we used the non-steroidal anti-inflammatory drug Naproxen. Warfarin was not used for these experiments, which are based on the fluorescence of the drug, since the fluorescence intensity of Warfarin depends on the presence of albumin, which may bias the release data. Like Warfarin, Naproxen has high affinity to albumin and may be used as a model drug for relatively low molecular weight drug molecules. Naproxen was added to six different hydrogel compositions for comparison of release kinetics data (FIG. 3). The results showed significantly slower release kinetics of the wild-type and mono-PEGylated albumin hydrogels in comparison to the other hydrogels. Multi-PEGylated albumin showed generally similar release kinetics to PEG and PEGylated fibrinogen hydrogels (used as non-affinity PEG-protein controls), with most of the drug released after about 1 hr. Purified mono-PEGylated albumin hydrogels, on the other hand, produced the slowest release kinetics, with only ~68% of the drug released after 5 hrs. Comparison between the $t_{50}$ of each system, i.e. the time at which 50% of the drug was released from the different hydrogels, is shown in Table 2. While no significant difference was observed between the release rates from PEG and PEGylated albumin hydrogels, the release was significantly slower in the case of wild-type albumin, and even slower in the case of mono-PEGylated albumin ($t_{50}$ of 1-2 hr, depending on the degree of purification).

TABLE 2

The time (in min) in which 50% of the drug is released from hydrogels composed of PEG and the following constituents: PEGylated albumin, PEGylated fibrinogen, wild-type albumin, mono-PEGylated albumin before purification, and mono-PEGylated albumin after purification.
Time at 50% Release (min) (n = 6)

| PEGylated Albumin | PEG | PEGylated Fibrinogen | PEG and Albumin | Mono-PEGylated Albumin | Purified MonoPEGylated Albumin |
|---|---|---|---|---|---|
| 7 ± 2 | 8 ± 2 | 4 ± 1 | 35 ± 23 | 59 ± 33 | 114 ± 47 |

Figure 4:
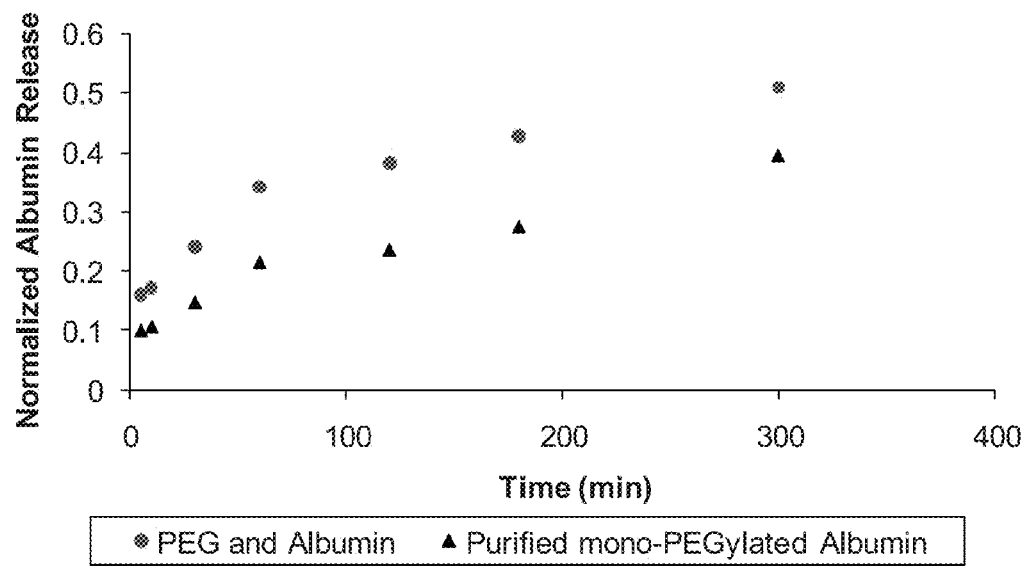
FIG. 4 shows percent of albumin released with time from hydrogels composed of PEG with wild-type albumin, and mono-PEGylated albumin after purification.

The difference between the release rates from mono-PEGylated and wild-type albumin may be explained by the slower release of albumin itself from the hydrogel in the case of conjugated albumin, as shown in FIG. 4.

In order to examine whether the drug release kinetics followed a Fickian diffusion model, we took the log of the release data (FIG. 3B). In diffusion controlled systems, the slope of the trend line is expected to be 0.5. It is possible to see in the graph that the hydrogels in the experiment may be divided to two main groups: PEG, PEGylated fibrinogen and multi-PEGylated albumin hydrogels, with a trend line slope of 0.39±0.03, and wild-type and mono-PEGylated albumin, with a slope of 0.19±0.03. The first values are relatively close to 0.5, with about 22% deviation from the model, in comparison of the second group, with about 63% deviation. Hence, the drug release from wild-type and mono-PEGylated albumin hydrogels is not dominated by diffusion. Some deviations from the model are probably caused by swelling and other physical phenomena during the release process, which were not accounted for in our experimental protocol.

Results of the release experiments with multi-PEGylated albumin hydrogels thus confirmed the previous results discussed above; due to the altered conformation of the protein after PEGylated, its affinity to the drug is significantly reduced and the drug's release from the hydrogel was similar to the release from PEG and PEGylated fibrinogen control hydrogels. In contrast, the mono-PEGylated albumin hydrogels, before and moreover after purification, showed a significantly slower release kinetics, probably based on the affinity of the drug to the protein. These findings confirm our hypothesis of reduced alterations to the tertiary albumin structure during the mono-PEGylation reaction, which preserves its drug binding ability. Another factor that may add to this effect may be the lower PEG content in the case of mono-PEGylated albumin, since PEG is a highly hydrophilic polymer and is considered to be a protein repellant due to its hydration shell.

For both mono-PEGylated albumin and wild-type albumin hydrogels, the release kinetics was clearly not based on diffusion. The drug molecules were released from mono-PEGylated albumin hydrogels slower than from the wild-type albumin hydrogels. The main reason for this was that in the case of albumin which was not covalently bound to the hydrogel matrix, there was a more significant diffusion of albumin molecules from the network, which decreases the ability of the hydrogel to bind the drug molecules by affinity. The kinetics of albumin release from the hydrogels during drug release experiments is shown in FIG. 4. It is possible to see in the graph that wild-type albumin was released from the hydrogel significantly faster than mono-PEGylated albumin. About 51% of the protein was released after 5 hours when it is not chemically conjugated to the hydrogel matrix, in comparison to about 39% in the case of mono-PEGylated protein. Further purification of the mono-PEGylated albumin system may be done to minimize the release of albumin from the hydrogel, thus improving its drug release properties. It is also important to note that the drug release experiments were conducted in solution, hence the release kinetics measured in vitro are expected to be significantly faster than when the hydrogels will be used in vivo.

Example 7

Release Kinetics of Various Drugs from Mono-PEGylated Albumin Hydrogels

Naproxen and Two Types of Insulin

The effect of drug molecular weight on the release kinetics of the drug from mono-PEGylated albumin hydrogels was examined using the drugs Naproxen and two types of insulin, Actrapid® and insulin detemir (Levemir®). As mentioned in Example 6, Naproxen has a relatively low molecular weight (230 Da), while Actrapid® and Levemir® are two types of regular human insulin with considerably higher molecular weights (5.8 and 5.9 kDa, respectively). Naproxen has a known affinity for albumin while regular insulin has none. However, insulin detemir was modified to have increased affinity for albumin. For the release experiments, both types of insulin were fluorescently labelled.

Figure 5:
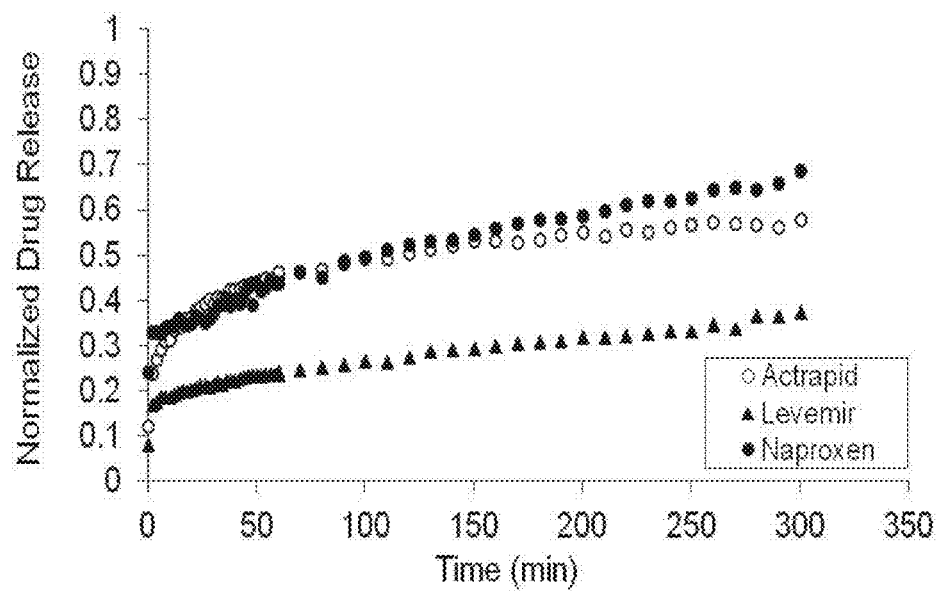
FIG. 5 shows normalized amount of the drugs Naproxen, Insulin ACTRAPID® and Insulin LEVEMIR® (Detemir) released with time from purified mono-PEGylated albumin hydrogels. Average drug release (last 30 min) was for Naproxen, 0.66±0.07 for ACTRAPID® 0.57±0.14 and 0.36±0.10 for LEVEMIR®.

The release kinetics of the three drugs from purified mono-PEGylated albumin hydrogels (10 kDa PEG) are shown in FIG. 5. As expected, it can be seen that the relatively low molecular weight drug, Naproxen, was released significantly faster than the high molecular weight drug, LEVEMIR®, although both of the drugs had high affinity to albumin (p-value<0.05). When comparing the two types of insulin, ACTRAPID® and LEVEMIR®, having similar molecular weights, it can be seen that LEVEMIR®, which has an increased affinity to albumin, was released significantly slower than ACTRAPID®, the non-modified insulin (p-value<0.05). The results showed that the release kinetics of drugs from the mono-PEGylated albumin hydrogels is affected both by the size of the drug molecules, i.e. their diffusion properties, and by the affinity of the drug to albumin. Although Naproxen has higher affinity to albumin, insulin detemir was released in a slower manner from the hydrogel, probably due to the big difference in molecular weight (230 Da and 5.9 kDa for Naproxen and insulin detemir, respectively). It is interesting to note that the release kinetics of Naproxen, a low molecular weight drug with high affinity to albumin, and ACTRAPID®, a high molecular weight drug with no affinity to albumin, are similar. This kind of experiments enables us to compare release kinetics of different drugs from the same hydrogel, and predict their relative in vivo release properties.

Example 8

Drug Release Kinetics from 10 kDa and 4 kDa Mono-PEGylated Albumin Hydrogels

Albumin was mono-PEGylated using linear PEG of two different molecular weights, 4 and 10 kDa. The mono-PEGylation process was verified using SDS-PAGE (FIG. 6A). It can be seen that mono-PEGylation of albumin with 10 kDa PEG resulted in a mixture of unreacted, mono-PEGylated and multi-PEGylated albumin species. For this reason we purified the mono-PEGylated species by gel chromatography, as described above in Materials and Methods. A similar PEGylation reaction of albumin with 4 kDa PEG also resulted in a mixture of PEGylated species, including unreacted, mono-PEGylated and multi-PEGylated albumin. In this case, it is possible to see albumin that was conjugated to one, two and three PEG-DA molecules. However, in both experiments with different PEG molecular weight, it is possible to see that a similar proportion of the albumin molecules reacted with only one PEG-DA molecule. Purification is more difficult in this case due to relatively small differences in molecular weight between the various PEGylated and unPEGylated species.

Figure 6B:
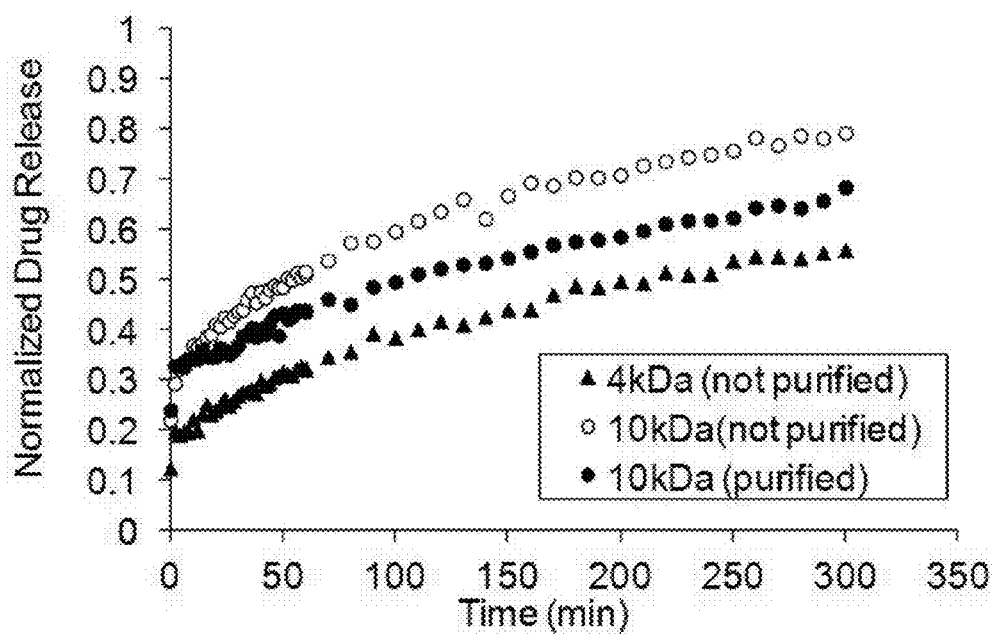

It is important to note that the mono-, di- or tri-PEGylated albumin species did not appear in the SDS-PAGE gel exactly according to their molecular weight as would be expected according to the marker line, but in a higher molecular weight level (FIG. 6A). This may be a result of the extended conformation and high hydrodynamic molecular volume of PEG relative to proteins. However, when comparing the molecular weights of 10 kDa mono-PEGylated albumin and 4 kDa mono-, di- or tri-PEGylated albumin, the marks appeared in the expected placements relative to one another. The SDS-PAGE results also indicated that the mono-PEGylation reaction, assumingly occurring with the Cys-34 residue, had a relatively low efficiency regardless of the PEG molecular weight. This may be explained by the location of the Cys-34 residue in a crevice on the surface of the albumin protein, which restricts its availability to reaction. It is also known that 30-50% of the albumin molecules in isolated albumin samples have Cys-34 blocked as a disulfide We used the drug Naproxen in drug release experiments in order to compare between release kinetics from 4 kDa mono-PEGylated albumin hydrogels and 10 kDa (purified and non-purified) mono-PEGylated albumin hydrogels (FIG. 6B). The release rate of the drug from 4 kDa mono-PEGylated albumin hydrogels was significantly slower than from 10 kDa mono-PEGylated albumin hydrogels, before and after purification (p-value<0.05), although the majority of PEG molecules in the hydrogel matrix are free 10 kDa PEG-DA added to the albumin in both cases (6.5%). This is another prove to our assumption that the affinity of the drugs to the albumin molecule, which was affected in this case by PEG conjugation to albumin, is the dominant factor in respect of the drug release kinetics, and not the matrix density. The differences between release kinetics from the 10 kDa and 4 kDa PEGylated albumin hydrogels may be explained by greater steric hindrance and higher hydrated molecular volume as the PEG molecular weight is increased.

The conjugated PEG molecule reduced the ability of the drug to approach its affinity sites on the protein. As the PEG molecular weight is reduced, the affinity of the drug to the conjugated protein is increased due to the lower steric repulsion, resulting in slower release kinetics from the hydrogel.

Example 9

Drug and Albumin Release During Hydrogel Enzymatic Degradation

Figure 7A:
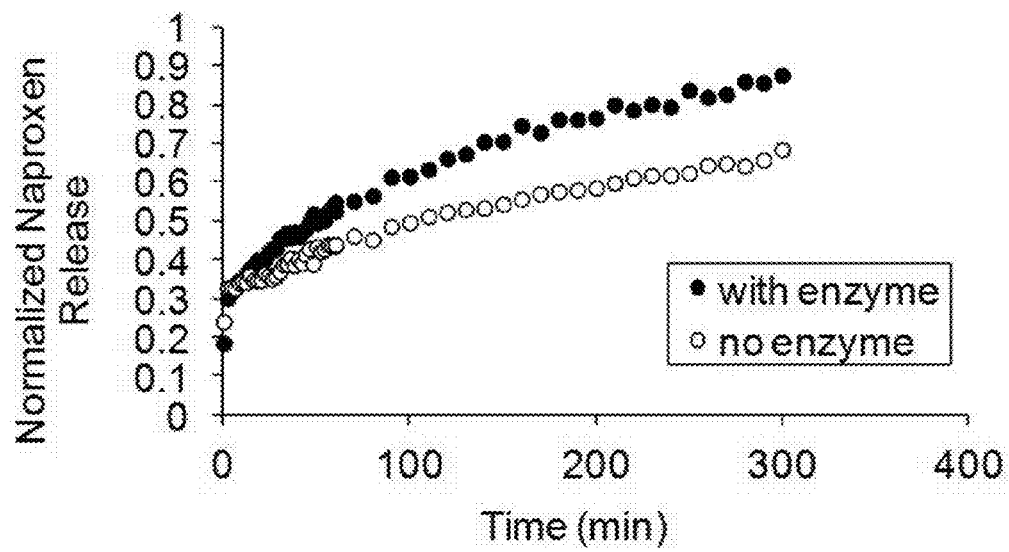
FIGS. 7A-7B show normalized amount of the drug Naproxen (A) and of albumin (B) released with time from purified 10 kDa mono-PEGylated albumin hydrogels, with and without the presence of the degrading enzyme Trypsin.
Figure 7B:
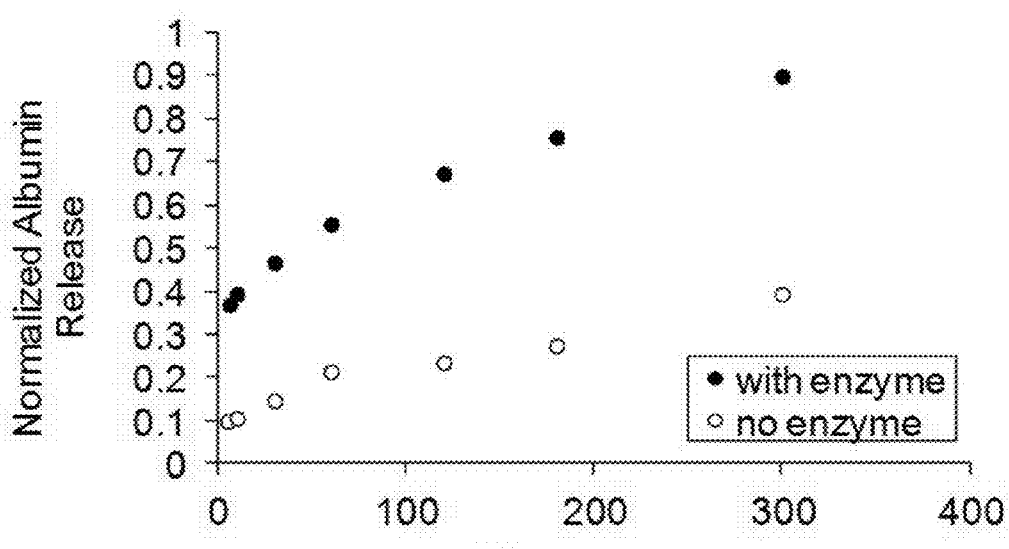

In the degradation experiments, we compared the release from purified 10 kDa mono-PEGylated albumin hydrogels to similar experiments in the presence of the enzyme Trypsin, which degrades various proteins, including albumin and fibrinogen (FIG. 7). The release of the model drug, Naproxen, from the hydrogels is shown in FIG. 7A. As expected, the release kinetics of the drug was faster during degradation, and more than 85% of the drug was released from the hydrogel matrix after 5 hours, in comparison to less than 70% released without the presence of the degrading enzyme. Similarly, FIG. 7B shows that the release of albumin from the hydrogel matrix was faster in the presence of the enzyme. It should be noted that also in this experiment, more than 85% of the albumin in the hydrogel was released from the matrix after 5 hours during degradation.

Figure 8:
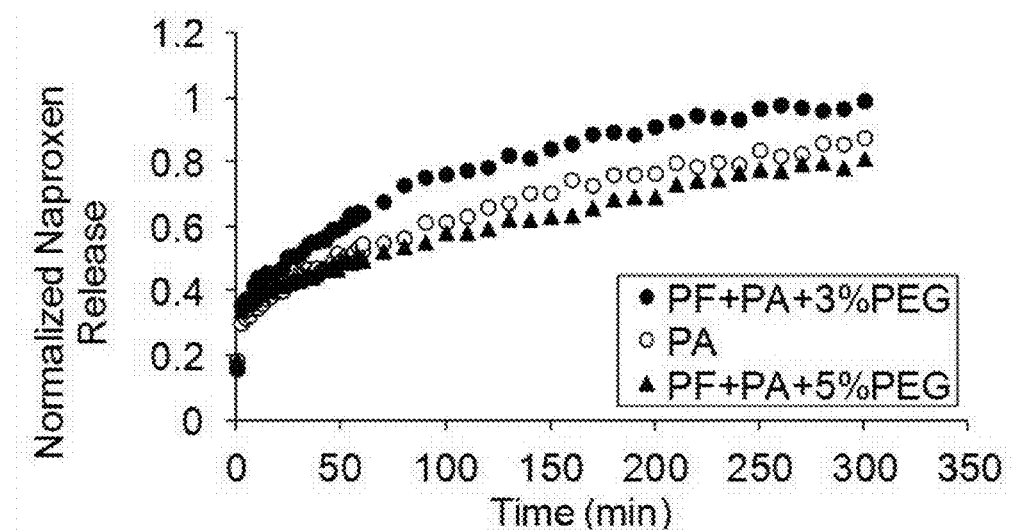
FIG. 8 shows normalized amount of the drug Naproxen released with time from hydrogels composed of: purified 10 kDa mono-PEGylated albumin with 6.5% free PEG-DA addition; purified 10 kDa mono-PEGylated albumin with PEGylated fibrinogen and 3% free PEG-DA addition; purified 10 kDa mono-PEGylated albumin with PEGylated fibrinogen and 5% free PEG-DA addition. Average Naproxen release during degradation (last 30 min) was 0.86±0.12 for Hydrogel composition PA, 0.80±0.10 for Hydrogel composition PA+PF+5% PEG and 0.97±0.06 for Hydrogel composition PA+PF+3% PEG.

Further degradation experiments were conducted using combined hydrogels which contained purified 10 kDa mono-PEGylated albumin with PEGylated fibrinogen (FIG. 8). In this case we used two different concentrations of free linear 10 kDa PEG-DA molecules added to the hydrogel matrix: 3% or 5%. In hydrogels not containing PEGylated fibrinogen, the free PEG-DA concentration was 6.5%. In FIG. 8 it is possible to see that the release kinetics of the model drug, Naproxen, were similar in the cases of mono-PEGylated albumin hydrogels with 6.5% free PEG-DA, and combined hydrogels containing 5% free PEG-DA. However, when the free PEG-DA addition to the hydrogels combining PEGylated albumin and fibrinogen was changed to 3%, the drug release kinetics was significantly faster.

The effect of enzymatic degradation on the release properties of the hydrogels were examined for two main purposes: to compare the release rate in the experiments presented so far to the rate in the presence of a degrading enzyme, and to assess the function of similar hydrogels for drug delivery during tissue regeneration. In vivo, albumin is degraded mostly in lysosomes. Its degradation is in general slower than the degradation rate of fibrinogen. In our previous work we have shown that this is also true when these proteins are multi-PEGylated and cross-linked in the form of hydrogels. In the present experiment we wanted to examine the effect of degradation on the release kinetics of drugs from mono-PEGylated albumin hydrogels. As expected, the results indicated that the drug is released faster in the presence of a degrading enzyme as a result of the degradation of the albumin protein, which decreases the affinity of the drug to the hydrogel. The protein is also a part of the hydrogel matrix, thus allowing faster diffusion into solution as the matrix is degraded. Without the enzyme, since most of the albumin is conjugated to the matrix, the protein is released more slowly out of the matrix and thus sustains the release of the drug. It is important to note that most of the albumin in the hydrogel is covalently conjugated to the matrix by mono-PEGylation, although complete purification is not achieved. Thus, there is also a small amount of un-conjugated albumin trapped in the matrix by physical means only. This may explain the release of a relatively small amount of albumin from the matrix even without the presence of a degrading enzyme.

The results also indicate on the ability to achieve the same release kinetics from a hydrogel containing mono-PEGylated albumin with 6.5% free PEG-DA, and from a hydrogel containing mono-PEGylated albumin with PEGylated fibrinogen and 5% free PEG-DA. This enables us to design a hydrogel with the desired combination of controlled release properties and tissue regeneration properties. Furthermore, we may control the release rate of drugs from the hydrogel matrix by using different free PEG-DA additions, due to the polymer's effect on the degradation rate and the cross-linking density of the matrix.

Example 10

3-D Cell Culture Experiment

Figure 9A:
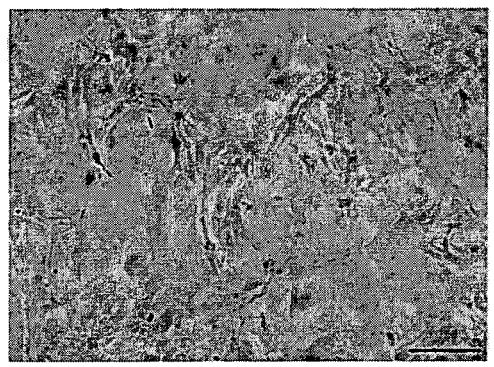
FIGS. 9A-F depict three dimensional cell culture in hydrogels composed of: PEGylated fibrinogen (day 3 microscopy image in A, day 7 histology image in E); 10 kDa mono-PEGylated albumin (day 4 microscopy image in B); PEGylated fibrinogen and mono-PEGylated albumin (8 mg/ml for each protein, day 3 microscopy image in C, day 7 histology image in F); and PEGylated fibrinogen and mono-PEGylated albumin (4 mg/ml for each protein, day 3 microscopy image in D).
Figure 9B:
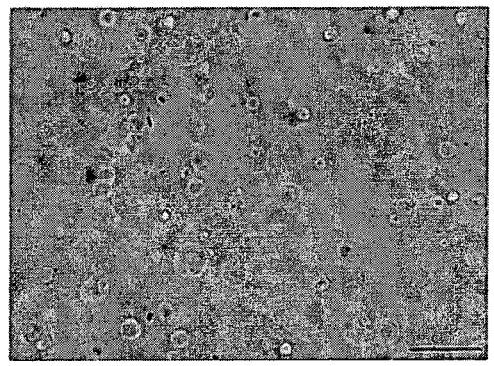
Figure 9C:
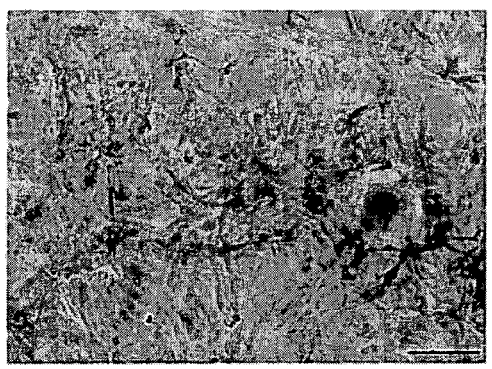
Figure 9D:
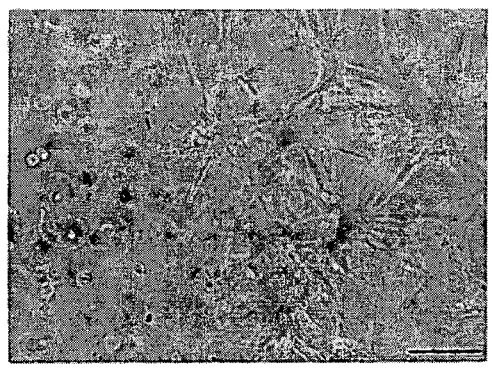
Figure 9E:
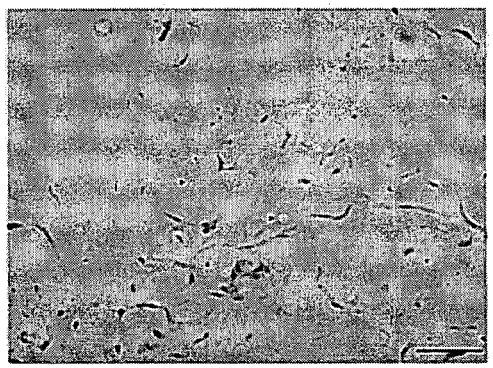
Figure 9F:
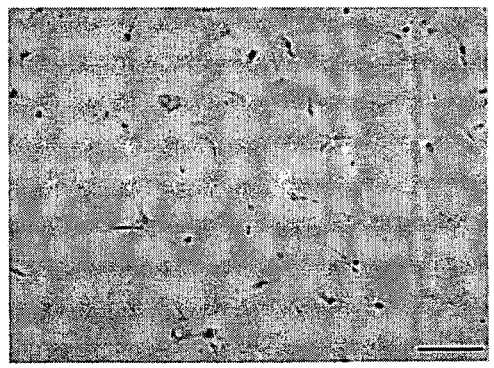

Human foreskin fibroblast (HFF) cells were dispersed into hydrogel precursor solutions of four different types, including PEGylated fibrinogen (8 mg/ml protein concentration); unpurified 10 kDa mono-PEGylated albumin (8 mg/ml, addition of 2% PEG-DA); PEGylated fibrinogen and mono-PEGylated albumin (8 mg/ml for each protein); and PEGylated fibrinogen and mono-PEGylated albumin (4 mg/ml for each protein, addition of 0.5% PEG-DA). Each solution containing encapsulated cells was then photopolymerized to produce a three dimensional (3-D) hydrogel. The cells spread well, and even formed some networks, in the cases of PEGylated fibrinogen, and PEGylated fibrinogen with mono-PEGylated albumin containing 8 mg/ml for each protein (FIGS. 9A, 9E, and FIGS. 9C, 9F, respectively). In the case of mono-PEGylated albumin hydrogels (FIG. 9B) the cells did not spread and remained round throughout the experiment, while in the hydrogels combining PEGylated fibrinogen with mono-PEGylated albumin containing 4 mg/ml for each protein (FIG. 9D) the construct contained areas of round cells and other areas of spread cells and networks of cells. In the last two cases, the hydrogels also degraded faster and histology after a week was not possible.

REFERENCES

Abuchowski A., T. van Es, N. C. Palczuk and F. F. Davis, Alteration of immunological properties of bovine serum albumin by covalent attachment of polyethylene glycol, J Biol Chem 252 (1977) 3578-3581.

Caliceti, P. and Veronese, F. M. Pharmacokinetic and biodistribution properties of poly(ethylene glycol)-protein conjugates, Adv Drug Deliv Rev (2003) 55, 1261-1277.

Christodoulou J., P. J. Sadler and A. Tucker, 1H NMR of albumin in human blood plasma: drug binding and redox reactions at Cys34, FEBS Lett 376 (1995) 1-5.

Dikovsky D., H. Bianco-Peled and D. Seliktar, The effect of structural alterations of PEG-fibrinogen hydrogel scaffolds on 3-D cellular morphology and cellular migration, Biomaterials 27 (2006) 1496-1506.

Drury J. L. and D. J. Mooney, Hydrogels for tissue engineering: scaffold design variables and applications, Biomaterials 24 (2003) 4337-4351.

Gayet J. C. and G. Fortier, Drug release from new bioartificial hydrogel, Artif Cells Blood Substit Immobil Biotechnol 23 (1995) 605-611.

Gayet J. C. and G. Fortier, High water content BSA-PEG hydrogel for controlled release device: Evaluation of the drug release properties, J Control Release 38 (1996) 177-184.

Gonen-Wadmany M., L. Oss-Ronen and D. Seliktar, Protein-polymer conjugates for forming photopolymerizable biomimetic hydrogels for tissue engineering, Biomaterials 28 (2007) 3876-3886.

Greenwald, R. B., Choe, Y. H., McGuire, J. and Conover, C. Effective drug delivery by PEGylated drug conjugates. Adv Drug Deliv Rev (2003) 55, 217-250.

Huynh D. P., M. K. Nguyen, B. S. Pi, M. S. Kim, S. Y. Chae, K. C. Lee, B. S. Kim, S. W. Kim and D. S. Lee, Functionalized injectable hydrogels for controlled insulin delivery, Biomaterials 29 (2008) 2527-2534.

Iza M., G. Stoianovici, L. Viora, J. L. Grossiord and G. Couarraze, Hydrogels of poly(ethylene glycol): mechanical characterization and release of a model drug, J Control Release 52 (1998) 41-51.

Kragh-Hansen U., V. T. Chuang and M. Otagiri, Practical aspects of the ligand-binding and enzymatic properties of human serum albumin, Biol Pharm Bull 25 (2002) 695-704.

Kratz F., Albumin as a drug carrier: Design of prodrugs, drug conjugates and nanoparticles, J Control Release (2008) 132, 171-183.

Lutolf M. P. and J. A. Hubbell, Synthesis and physicochemical characterization of end-linked poly(ethylene glycol)-co-peptide hydrogels formed by Michael-type addition, Biomacromolecules 4 (2003) 713-722.

Murayama K. and M. Tomida, Heat-induced secondary structure and conformation change of bovine serum albumin investigated by Fourier transform infrared spectroscopy, Biochemistry 43 (2004) 11526-11532.

Murray J. B., L. Brown, R. Langer and M. Klagsburn, A micro sustained release system for epidermal growth factor, In Vitro 19 (1983) 743-748.

Nag A., G. Mitra and P. C. Ghosh, A colorimetric assay for estimation of polyethylene glycol and polyethylene glycolated protein using ammonium ferrothiocyanate, Anal Biochem 237 (1996) 224-231.

Peppas N. A., P. Bures, W. Leobandung and H. Ichikawa, Hydrogels in pharmaceutical formulations, Eur J Pharm Biopharm 50 (2000) 27-46.

Peters T., Jr., Serum albumin. Adv Protein Chem (1985) 37, 161-245.

Peters T., Jr., Serum albumin: recent progress in the understanding of its structure and biosynthesis, Clin Chem 23 (1977) 5-12.

Veronese F. M. and G. Pasut, PEGylation, successful approach to drug delivery, Drug Discov Today 10 (2005) 1451-1458.

Wacker B. K., E. A. Scott, M. M. Kaneda, S. K. Alford and D. L. Elbert, Delivery of sphingosine 1-phosphate from poly(ethylene glycol) hydrogels, Biomacromolecules 7 (2006) 1335-1343.

The invention claimed is:

1. A hydrogel system for controlled release delivery of a therapeutic agent, wherein said hydrogel comprises mainly mono-PEGylated albumin molecules, and each of said mono-PEGylated albumin molecules is composed of an albumin molecule conjugated to a single Poly(ethylene glycol) diacrylate (PEG-DA) having a molecular weight in the range of 4 kDa to 10 kDa, the first acrylate group being attached to said albumin molecule and the second acrylate group being attached to a matrix.

2. The hydrogel system of claim 1, wherein said first acrylate group of said PEG-DA is covalently attached to a cysteine residue of said albumin.

3. The hydrogel system of claim 1, wherein said matrix is composed of a polymer identical to the PEG of the PEG-conjugated albumin molecules.

4. A hydrogel composition for sustained release of a therapeutic agent comprising a hydrogel system according to claim 1 and said therapeutic agent.

5. The hydrogel composition of claim 4, wherein said therapeutic agent is bound to said albumin.

6. The hydrogel composition of claim 5, wherein said therapeutic agent is a disinfectant, a chemotherapeutic agent, an antimicrobial agent, an antiviral agent, a hemostatic agent, an antiphlogistic agent, an anesthetic, an analgesic, a nutritional supplement, a growth factor, a peptide, a polypeptide, a plasma derivative protein, a lipid or an enzyme.

7. The hydrogel composition of claim 4, further comprising a bioactive polypeptide exhibiting tissue regeneration properties, thus allowing a combination of sustained release of the therapeutic agent and tissue regeneration.

8. An implant comprising the hydrogel composition as defined in claim 4.

9. A method of generating the hydrogel system of claim 1, the method comprising:
(a) covalently attaching albumin to a single Poly(ethylene glycol) diacrylate (PEG-DA) having a molecular weight in the range of 4 kDa to 10 kDa through the first acrylate group of said PEG-DA, to thereby obtain a PEG-conjugated albumin precursor molecule;
(b) mixing the PEG-conjugated albumin precursor molecule of (a) with a PEG comprising a functional group capable of copolymerizing with the second acrylate group of said PEG-DA of said precursor molecule;
(c) subjecting the mixture of (b) to copolymerization, to thereby generate said hydrogel system comprising a matrix to which a plurality of monoPEG-conjugated albumin molecules are linked via said second acrylate group of said PEG-DA.

10. The method of claim 9, wherein the PEG comprising a functional group capable of copolymerizing with the second acrylate group of the PEG-DA of said precursor molecule is PEG-DA.

11. The method of claim 9, further comprising adding a therapeutic agent.

12. The method of claim 9, wherein the copolymerization is initiated by ultraviolet illumination, optionally in the presence of a photoinitiator.

* * * * *